(12) United States Patent
Wulfman

(10) Patent No.: US 8,914,130 B2
(45) Date of Patent: Dec. 16, 2014

(54) IMPLANTABLE LEAD WITH IN-LEAD SWITCHING ELECTRONICS

(75) Inventor: David R. Wulfman, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1065 days.

(21) Appl. No.: 12/233,345

(22) Filed: Sep. 18, 2008

(65) Prior Publication Data

US 2009/0088812 A1   Apr. 2, 2009

Related U.S. Application Data

(60) Provisional application No. 60/975,743, filed on Sep. 27, 2007, provisional application No. 60/976,702, filed on Oct. 1, 2007.

(51) Int. Cl.
*A61N 1/05* (2006.01)
*A61N 1/375* (2006.01)
*A61N 1/372* (2006.01)

(52) U.S. Cl.
CPC .............. *A61N 1/056* (2013.01); *A61N 1/0563* (2013.01); *A61N 1/375* (2013.01); *A61N 1/37205* (2013.01)
USPC ......... 607/116; 607/5; 607/9; 607/15; 607/37

(58) Field of Classification Search
USPC ........................................................ 607/122
See application file for complete search history.

(56) References Cited

U.S. PATENT DOCUMENTS

| | | |
|---|---|---|
| 4,432,372 A | 2/1984 | Monroe et al. |
| 4,485,813 A | 12/1984 | Anderson et al. |
| 4,566,456 A | 1/1986 | Koning et al. |
| 4,708,143 A | 11/1987 | Schroeppel |
| 4,791,935 A | 12/1988 | Baudino et al. |

(Continued)

FOREIGN PATENT DOCUMENTS

| | | |
|---|---|---|
| JP | 61-90068 A | 7/1994 |
| JP | 2006/516449 A | 7/2006 |

(Continued)

OTHER PUBLICATIONS

"International Application Serial No. PCT/US2008/010859, International Search Report mailed Dec. 8, 2008", 4 pgs.

(Continued)

*Primary Examiner* — Kennedy Schaetzle
(74) *Attorney, Agent, or Firm* — Schwegman, Lundberg & Woessner, P.A.

(57) ABSTRACT

One example includes an implantable lead including an elongate lead body which includes a proximal portion and a distal portion. In the example, the lead includes a coupler configured to couple to an implantable medical device. The lead includes a first conductor, coupled to the coupler, and extending away from the coupler at least partially through the lead. The lead includes a first electrode, located on the lead away from the coupler and a first switch, located on the lead away from the coupler, the first switch configured to control conductivity between the conductor and the electrode. The lead also includes a first controller circuit, coupled to the conductor and including a first multiplexer circuit configured to multiplex over the conductor a first signal and a second signal, the first controller circuit configured to control the first switch based at least on the first signal.

25 Claims, 18 Drawing Sheets

(56) References Cited

U.S. PATENT DOCUMENTS

| | | | |
|---|---|---|---|
| 4,967,755 A | | 11/1990 | Pohndorf et al. |
| 5,186,169 A | | 2/1993 | Schaldach |
| 5,275,171 A | | 1/1994 | Barcel |
| 5,324,326 A | | 6/1994 | Lubin |
| 5,324,327 A | | 6/1994 | Cohen |
| 5,325,870 A | * | 7/1994 | Kroll et al. .............. 607/122 |
| 5,336,253 A | | 8/1994 | Gordon et al. |
| 5,411,532 A | | 5/1995 | Mortazavi |
| 5,423,866 A | | 6/1995 | Ekwall |
| 5,423,873 A | * | 6/1995 | Neubauer et al. .............. 607/68 |
| 5,431,692 A | | 7/1995 | Hansen et al. |
| 5,593,430 A | | 1/1997 | Renger |
| 5,651,767 A | | 7/1997 | Schulman et al. |
| 5,660,163 A | | 8/1997 | Schulman et al. |
| 5,728,281 A | | 3/1998 | Holmstrom et al. |
| 5,824,018 A | | 10/1998 | Dreher et al. |
| 5,843,135 A | | 12/1998 | Weijand et al. |
| 5,999,848 A | | 12/1999 | Gord et al. |
| 6,043,437 A | | 3/2000 | Schulman et al. |
| 6,144,866 A | | 11/2000 | Miesel et al. |
| 6,221,012 B1 | | 4/2001 | Maschke et al. |
| 6,223,081 B1 | | 4/2001 | Kerver |
| 6,418,348 B1 | | 7/2002 | Witte |
| 6,421,567 B1 | * | 7/2002 | Witte .............. 607/122 |
| 6,473,653 B1 | * | 10/2002 | Schallhorn et al. .............. 607/116 |
| 6,529,777 B1 | | 3/2003 | Hedberg et al. |
| 6,754,530 B2 | | 6/2004 | Bakels et al. |
| 6,804,552 B2 | | 10/2004 | Thompson |
| 6,859,667 B2 | | 2/2005 | Goode, Jr. |
| 6,875,180 B2 | | 4/2005 | Weiner et al. |
| 7,016,726 B1 | | 3/2006 | Picardo et al. |
| 7,139,613 B2 | | 11/2006 | Reinke et al. |
| 7,174,219 B2 | | 2/2007 | Wahlstrand et al. |
| 7,177,698 B2 | | 2/2007 | Klosterman et al. |
| 7,190,245 B2 | | 3/2007 | Receveur et al. |
| 7,225,025 B2 | | 5/2007 | Goode |
| 7,236,834 B2 | | 6/2007 | Christopherson et al. |
| 7,493,174 B2 | | 2/2009 | Belalcazar et al. |
| 7,616,991 B2 | | 11/2009 | Mann et al. |
| 2002/0143258 A1 | | 10/2002 | Weiner et al. |
| 2003/0088303 A1 | | 5/2003 | Goode |
| 2003/0149456 A1 | | 8/2003 | Rottenberg et al. |
| 2005/0043768 A1 | | 2/2005 | Goode |
| 2005/0165456 A1 | | 7/2005 | Mann et al. |
| 2006/0122679 A1 | | 6/2006 | Wengreen et al. |
| 2006/0287682 A1 | | 12/2006 | Cohen et al. |
| 2007/0293903 A1 | | 12/2007 | Bohn et al. |
| 2009/0088811 A1 | | 4/2009 | Wulfman |
| 2010/0016918 A1 | | 1/2010 | Mann et al. |

FOREIGN PATENT DOCUMENTS

| | | |
|---|---|---|
| WO | WO-99/12607 A1 | 3/1999 |
| WO | WO-99/12607 A1 | 3/1999 |
| WO | WO-99/13561 A1 | 3/1999 |
| WO | WO-99/13561 A1 | 3/1999 |
| WO | WO-2004/067081 A2 | 8/2004 |
| WO | WO-2006/069322 A2 | 6/2006 |
| WO | WO-2006/069323 A1 | 6/2006 |
| WO | WO-2009/042063 A1 | 4/2009 |

OTHER PUBLICATIONS

"International Application Serial No. PCT/US2008/010859, Written Opinion mailed Dec. 8, 2008", 8 pgs.

"Low-Profile Connectors (IS-1) for Implantable Cardiac Pacemakers", The European Standard EN 50077; The British Standard Published under the authority of the Standards Board, (1993), 15 pgs.

Carr, W. N., et al., "Integrated Pressure Sensor With Remote Power Source and Remote Readout", *The 8th International Conference on Solid-State Sensors and Actuators and Eurosensors IX, Digest of Technical Papers*, vol. 1, Stockholm, Sweden, (Jun. 1995), 624-627.

Chau, H-L., "An Ultraminiature Solid-State Pressure Sensor for a Cardiovascular Catheter", *IEEE Transactions on Electron Devices*, 35(12), (Dec. 1988), 2355-2362.

Ji, J., "An Ultraminiature CMOS Pressure Sensor for a Multiplexed Cardiovascular Catheter", *IEEE Transactions on Electron Devices*, 39(10), (Oct. 1992), 2260-2267.

Lau, C., "Chapter 13—Central Venous Oxygen Saturation and Other Sensors", *Rate Adaptive Cardiac Pacing: Single and Dual Chamber*, Futura Publishing Company, Inc., Mount Kisco, NY, (1993), 181-194.

Laudon, M. K., "Chapter 11—Pulse Output", *Design of Cardiac Pacemakers*, Webster, J. G., Editor, IEEE Press, New York, (1995), 251-276.

Sakurai, T., et al., "An Improved Dispenser Cathode", *International Electron Devices Meeting*, Technical Digest, (Dec. 1984), 322-325.

Shuros, A. C., et al., "Method and Device for Simulated Exercise", U.S. Appl. No. 11/559,131, filed Nov. 13, 2006, 32 pgs.

Spiegel, E. "A CMOS Sensor and Signal Conversion Chip for Monitoring Arterial Blood Pressure and Temperature", *IEEE International Solid-State Circuits Conference.*, (Feb. 20, 1992), 126-127.

Wagner, B. K., "Chapter 6—Electrodes, Leads, and Biocompatibility", *Design of Cardiac Pacemakers*, Webster, J. G., Editor, IEEE Press, New York, (1995), 132-160.

"U.S. Appl. No. 12/233,333, Examiner Interview Summary mailed Mar. 23, 2012", 3 pgs.

"U.S. Appl. No. 12/233,333, Examiner Interview Summary mailed Aug. 17, 2012", 1 pg.

"U.S. Appl. No. 12/233,333, Final Office Action mailed Jun. 6, 2012", 17 pgs.

"U.S. Appl. No. 12/233,333, Notice of Allowance mailed Aug. 17, 2012", 9 pgs.

"U.S. Appl. No. 12/233,333, Response filed Mar. 30, 2012 to Non Final Office Action mailed Jan. 9, 2012", 16 pgs.

"U.S. Appl. No. 12/233,333, Response filed Aug. 6, 2012 to Final Office Action mailed Jun. 6, 2012", 11 pgs.

"European Application Serial No. 08834304.1, Office Action mailed Aug. 14, 2012", 5 pgs.

"Japanese Application Serial No. 2010-526907, Examiners Decision of Final Refusal mailed Jun. 18, 2012", (w/ English Translation), 7 pgs.

"Japanese Application Serial No. 2010-526907, Office Action mailed Feb. 123, 2012", (w/ English Translation), 10 pgs.

"Japanese Application Serial No. Response filed Apr. 26, 2012 to Office Action mailed Feb. 13, 2012", (w/English Translation of Amended Claims), 9 pgs.

Hambley, Allan R., *Electrical Engineering Principles and Applications*, Fifth Edition, (1997), pp. 1-35.

"U.S. Appl. No. 12/233,333, Non-Final Office Action Mailed Jan. 9, 2012", 17 pgs.

"U.S. Appl. No. 12/233,333, Response filed Nov. 7, 2011 to Restriction Requirement mailed Oct. 12, 2011", 10 pgs.

"U.S. Appl. No. 12/333,333, Restriction Requirement mailed Oct. 12, 2011", 6 pgs.

* cited by examiner

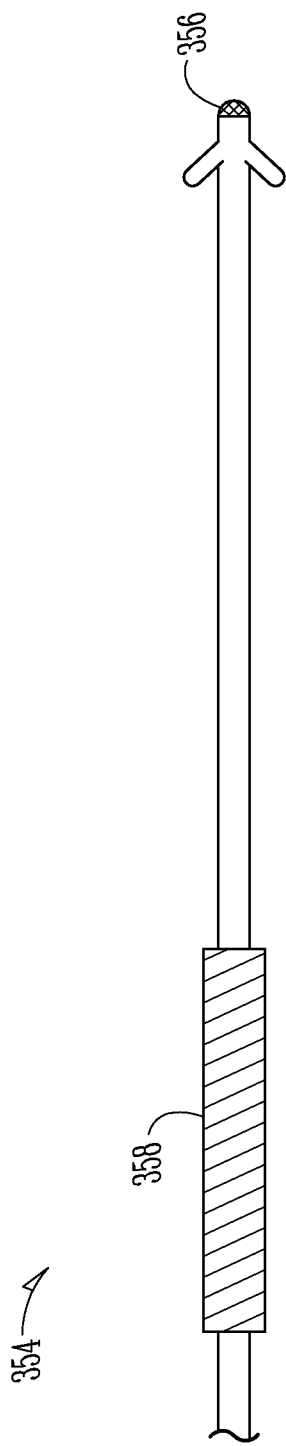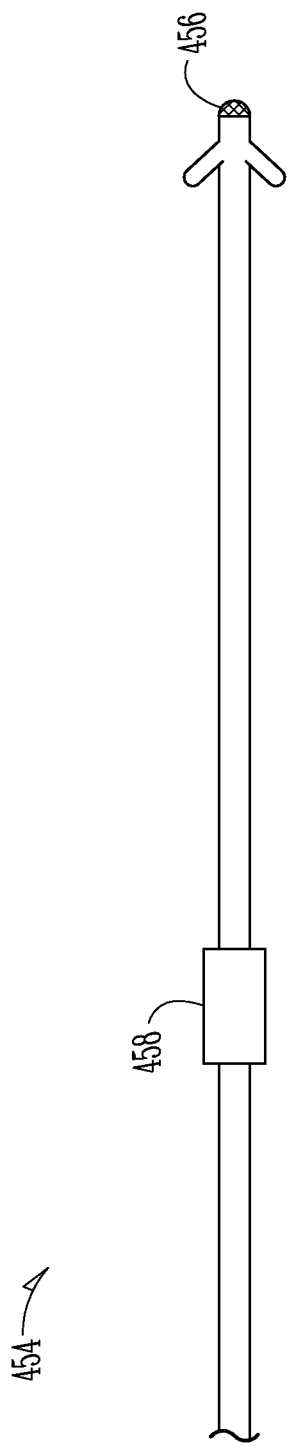

IMPLANTABLE LEAD WITH IN-LEAD SWITCHING ELECTRONICS

CROSS REFERENCE TO RELATED MATTERS

This application claims the benefit under 35 U.S.C. 119(e) of U.S. Provisional Patent Application Ser. No. 60/975,743, entitled "Implantable Lead with an Electrostimulation Capacitor," filed on Sep. 27, 2007; and U.S. Provisional Patent Application Ser. No. 60/976,702, entitled "Implantable Lead with Electronics," filed on Oct. 1, 2007, each of which is incorporated herein by reference in its entirety.

TECHNOLOGY FIELD

This document relates generally to the field of implantable medical devices and more particularly, but not by way of limitation, to an implantable lead with electronics.

BACKGROUND

Implantable medical devices interact with patients. For example, cardiac rhythm management devices provide electrical pulses to a patient to improve functioning of the cardiovascular system. A cardiac rhythm management device may be coupled to the heart by an intravascular lead including one or more electrodes at its distal end, which are typically connected by individual conductors to a connector at its proximal end. The connector is generally connected to a header of an electronics unit of the cardiac rhythm management device.

OVERVIEW

The present inventor has recognized that certain methods of using intravascular or other leads or catheters demand a smaller lead diameter, such as for inserting a multi-electrode lead (e.g., with three or four electrodes) into a coronary sinus or great cardiac vein, for example. Such an arrangement can be used, for example, for providing cardiac resynchronization therapy (CRT) to the left side of the heart, such as the left ventricle. However, more complex intravascular leads (e.g., with multiple electrodes, defibrillation shock electrodes, or the like) tend to be larger in diameter. This is because each electrode is generally accompanied by an individual conductor extending from the electrode to the proximal end of the lead. Moreover, each conductor generally uses a gauge (diameter) to accommodate the power density of the electrical energy being delivered via the conductor to the electrode. For example, to deliver a pacing or cardiac resynchronization electrostimulation pulse from (1) an electrostimulation storage capacitor located in an implantable cardiac function management device that is coupled to the proximal end of the lead to (2) an electrode located away from the proximal end of the lead, such as at a distal portion of the lead, the intervening lead conductor is generally sized to handle the power conducted during the pacing or CRT electrostimulation pulse—a period of time that is generally only tens of milliseconds in duration. However, such electrostimulation pulses typically have a very low duty cycle. For example, successive pacing or CRT electrostimulation pulses can be separated by a period of time that is on the order of a second.

Accordingly, the present inventor has recognized that by locating a small-sized electrostimulation capacitor away from the proximal portion of the lead, such as at a distal portion of the intravascular lead—in close proximity to the electrode that will deliver the electrostimulation to the tissue—the conductor used to charge the electrostimulation capacitor can be made smaller in diameter, because the electrostimulation energy can be carried by the conductor substantially over the full period of time between electrostimulation pulses. The electrostimulation capacitor located away from the proximal end of the lead, such as on the distal portion of the lead, can also potentially be charged using a higher voltage than an electrostimulation capacitor located in the cardiac function management device; there will be less resistive drop between an electrostimulation capacitor located on the distal portion of the lead and the electrode, which is also located on the distal portion of the lead.

Moreover, the present inventor has recognized that one or more controller circuits can also be embedded in the lead away from its proximal end, such as at a distal portion of the intravascular lead, such as to control one or more switches that selectively couple a distal lead electrostimulation capacitor to one or more electrodes that are also located on the distal portion of the intravascular lead. Moreover, such controller circuit(s) can even communicate with the cardiac function management device, or each other, using the same conductor that carries the electrostimulation energy from the cardiac function management device to the electrostimulation capacitor(s) located on the distal portion of the lead. Such a configuration can even be used to implement a single-conductor lead, if desired, that includes at a distal portion multiple electrodes that can be individually operated to provide electrostimulation energy as desired.

Some examples provide a lead which can receive multiplexed communications from a device to which it is coupled. Additional examples provide a lead which can also provide multiplexed communications to a device to which it is coupled. Such examples can provide multiple loads in a lead, such as electrodes or sensors, without adding conductors for each respective load. These examples can offer smaller lead diameters, and are therefore easier to work with during surgical implantation. Several examples are provided.

Example 1 describes an apparatus comprising an implantable lead. In this example, the implantable lead comprises an elongate lead body. The elongate lead body comprises a proximal portion and a distal portion. A coupler is located at the proximal portion of the lead body. The coupler is configured to be coupled to an implantable medical device. A conductor extends from the coupler at the proximal portion of the lead body to a distal portion of the lead body. A first electrode is located at the distal portion of the lead body. A first electrostimulation capacitor is located at the distal portion of the lead body. The first electrostimulation capacitor includes a capacitance value that is large enough to store an electrostimulation charge of an electrostimulation energy. The electrostimulation energy is large enough to perform electrostimulation of tissue. At least one first switch is located at the distal portion of the lead body and coupled to the conductor. The at least one first switch is configured to selectively couple the first electrostimulation capacitor to the first electrode during a stimulating state. The at least one first switch is configured to selectively couple the first electrostimulation capacitor to the conductor during a charging state.

In Example 2, the apparatus of Example 1 is optionally configured such that the first electrostimulation capacitor includes a capacitance value that is large enough to store an electrostimulation charge of an electrostimulation energy that is large enough to evoke contraction of myocardial tissue.

In Example 3, the apparatus of one or any combination of Examples 1-2 optionally comprises a second electrostimulation capacitor located at the distal portion of the lead body. The second electrostimulation capacitor includes a capacitance value that is large enough to store an electrostimulation charge sized to evoke electrostimulation of tissue. At least one second switch is located at the distal portion of the lead body and coupled to the conductor. The at least one second switch is configured to selectively couple the second electrostimulation capacitor to a second electrode during a stimulating state and to selectively couple the second electrostimulation capacitor to the conductor during a charging state.

In Example 4, the apparatus of one or any combination of Examples 1-3 optionally is configured such that a gauge size of the conductor is smaller than a gauge size needed to deliver the electrostimulation energy at a particular voltage from the coupler to the tissue without using the first electrostimulation capacitor to store the electrostimulation energy at the distal portion of the lead body at the particular voltage.

In Example 5, the apparatus of one or any combination of Examples 1-4 optionally is configured such that the lead body comprises only one conductor extending from the proximal portion of the lead body to the distal portion of the lead body.

In Example 6, the apparatus of one or any combination of Examples 1-5 optionally comprises a power converter located at the distal portion of the lead body and coupled to the first electrostimulation capacitor.

In Example 7, the apparatus of one or any combination of Examples 1-6 optionally comprises a switching circuit that is configured to electrically disconnect the distal portion of the lead body from the implantable medical device during delivery of an electrostimulation.

In Example 8, the apparatus of one or any combination of Examples 1-7 optionally is configured such that the lead comprises a controller circuit, located at the distal portion of the lead body, the controller circuit coupled to the conductor and configured to control charging of the electrostimulation capacitor from the implantable medical device via the conductor.

In Example 9, the apparatus of one or any combination of Examples 1-8 optionally comprises a powering capacitor, located at the distal portion of the lead body, the powering capacitor coupled to the controller circuit. At least one second switch is located at the distal portion of the lead body and coupled to the conductor, the at least one second switch configured to selectively couple the powering capacitor to the conductor in a charging state and to selectively couple the powering capacitor to the controller circuit during a controller powering state to power the controller circuit.

In Example 10, the apparatus of one or any combination of Examples 1-9 optionally comprises a controller circuit, located at the distal portion of the lead body, the controller circuit coupled to the at least one first switch to control coupling of the electrostimulation capacitor to an electrostimulation location via the first electrode in response to a communication signal received from the implantable medical device via the conductor.

Example 11 describes a method comprising: delivering electrical energy from a power source in an implantable medical device to an elongate lead body including a proximal portion and a distal portion such that a conductor located in the lead body and extending from the proximal portion to the distal portion conducts energy from the power source and through the lead body; storing electrical energy, at a location that is at the distal portion of the lead body, in an amount that is enough to evoke electrostimulation of tissue; and selectively switching, at the distal portion of the lead body, to deliver the stored energy to tissue.

In Example 12, the method of Example 11 optionally comprises: communicating encoded information from the implantable medical device to a control circuit that is located at the distal portion of the lead; and using the information at the control circuit to control the selectively switching, at the distal portion of the lead body, to deliver the stored energy to tissue.

In Example 13, the method of one or any combination of Examples 11-12 optionally comprises storing electrical energy, at a location that is at the distal portion of the lead body, in an amount that is enough to power the control circuit during a time when the control circuit is unconnected to the implantable medical device.

In Example 14, the method of one or any combination of Examples 11-13 optionally is performed such that the act of storing electrical energy, at a location that is at the distal portion of the lead body, in an amount that is enough to evoke electrostimulation of tissue, comprises storing electrical energy using a capacitor at the location that is at the distal portion of the lead body.

In Example 15, the method of one or any combination of Examples 11-14 optionally comprises storing electrical energy, at a location that is at the distal portion of the lead body, in an amount that is enough to power electronic circuitry located at the distal portion of the lead body during a time period when the electronic circuitry located at the distal portion of the lead body is electrically isolated from the implantable medical device.

In Example 16, the method of one or any combination of Examples 11-15 optionally comprises storing electrical energy, at a location that is at the distal portion of the lead body, in an amount that is enough to power a controller circuit located at the distal portion of the lead body during a time period when the controller circuit located at the distal portion of the lead body is electrically isolated from the implantable medical device.

In Example 17, the method of one or any combination of Examples 11-16 optionally comprises electrically disconnecting the distal portion of the lead body from the implantable medical device during delivery of an electrostimulation.

In Example 18, the method of one or any combination of Examples 11-17 optionally comprises performing the method using a lead that comprises only one conductor extending from the proximal portion of the lead body to the distal portion of the lead body.

Example 19 describes an apparatus comprising an intravascular implantable cardiac function management lead, comprising an elongate lead body comprising a proximal portion and a distal portion. In this example the lead comprises a coupler, located at the proximal portion of the lead body, the coupler configured to be coupled to an implantable cardiac function management device. A first electrode is located at the distal portion of the lead body. A conductor extends from the coupler at the proximal portion of the lead body to a distal portion of the lead body, wherein a gauge size of the conductor is smaller than a gauge size needed to deliver the electrostimulation energy at a particular voltage from the coupler to the tissue without using the first electrostimulation capacitor to store the electrostimulation energy at the distal portion of the lead body at the particular voltage. A power converter is located at the distal portion of the lead body and coupled to the first electrostimulation capacitor. A first electrostimulation capacitor is located at the distal portion of the lead body, the first electrostimulation capacitor including a capacitance value that is large enough to store an electrostimulation charge of an electrostimulation energy, wherein the electrostimulation energy is large enough to perform electrostimulation of tissue to evoke a resulting heart chamber contraction. A controller circuit is located at the distal portion of the lead body, the controller circuit coupled to the conductor and configured to control charging of the electrostimulation capacitor from the implantable medical device via the conductor. A powering capacitor is located at the distal portion of the lead body, the powering capacitor coupled to the controller circuit At least one second switch is located at the distal portion of the lead body and coupled to the conductor, the at least one second switch configured to selectively couple the powering capacitor to the conductor in a charging state and to selectively couple the powering capacitor to the controller circuit during a controller powering state to power the controller circuit. At least one first switch is located at the distal portion of the lead body and coupled to the conductor, the at least one first switch configured to selectively couple the first electrostimulation capacitor to the first electrode during a stimulating state, the at least one first switch configured to selectively couple the first electrostimulation capacitor to the conductor during a charging state.

In Example 20, the apparatus of Example 19 is optionally configured such that the lead body comprises only one conductor extending from the proximal portion of the lead body to the distal portion of the lead body.

Example 21 describes an apparatus. In this example, the apparatus comprises an implantable lead. The lead comprises an elongate lead body comprising a proximal portion and a distal portion. A coupler is located at the proximal portion of the elongate lead body. The coupler is configured to couple to an implantable medical device. A first conductor is coupled to the coupler, and extends away from the coupler at least partially through the lead along the elongate lead body. A first electrode is located on the lead away from the coupler. A first switch is located on the lead away from the coupler. The first switch is configured to control conductivity between the conductor and the electrode. A first controller circuit is located on the lead away from the coupler. The first controller circuit is coupled to the conductor and includes a first multiplexer circuit configured to multiplex over the conductor a first signal and a second signal. The first controller circuit is configured to control the first switch based at least on the first signal.

In Example 22, the apparatus of Example 21 is optionally configured such that the lead body comprises only one conductor extending from the proximal portion of the lead body to the distal portion of the lead body.

In Example 23, the apparatus of one or any combination of Examples 21-22 optionally comprises a sensor, located at the distal portion of the lead body and coupled to the first controller circuit, wherein the first signal includes sensor information associated with the sensor.

In Example 24, the apparatus of one or any combination of Examples 21-23 optionally comprises a second switch configured to control conductivity between the conductor and a second electrode.

In Example 25, the apparatus of one or any combination of Examples 21-24 optionally comprises a second controller circuit coupled to the conductor and including a second multiplexer circuit configured to multiplex over the conductor the first signal and the second signal, the second controller circuit configured to control the second switch based at least on the first signal.

In Example 26, the apparatus of one or any combination of Examples 21-25 optionally is configured to control the first switch based at least on the first signal, wherein the first signal includes a pulse delivery program.

In Example 27, the apparatus of one or any combination of Examples 21-26 optionally is configured such that the first controller circuit includes a timer circuit, and wherein the pulse delivery program includes a specified delay used by the timer to control the first switch.

In Example 28, the apparatus of one or any combination of Examples 21-27 optionally is configured such that the first controller circuit includes a timer circuit, and wherein the pulse delivery program is used by the timer to control the first switch.

In Example 29, the apparatus of one or any combination of Examples 21-28 optionally is configured such that the multiplexer is configured to provide the second signal that includes a charging signal for an electrostimulation capacitor located on the lead.

Example 30 describes a method comprising: multiplexing a first signal and a second signal for conduction between an implantable medical device and a portion of an elongate lead body coupled to, and located away from, the implantable medical device; and using at least the first signal, controlling a switching at the portion of the lead body located away from the implantable medical device.

In Example 31, the method of Example 30 optionally comprises using at least the first signal, controlling the switching at the portion of the lead body located away from the implantable medical device for transmitting an electrostimulation or defibrillation energy from the implantable medical device to a first electrode located at the portion of the lead body located away from the implantable medical device.

In Example 32, the method of one or any combination of Examples 30-31 optionally comprises powering a first controller circuit, located at the portion of the lead body located away from the implantable medical device, using energy stored at the portion of the lead body located away from the implantable medical device using the second signal, the powering occurring when the first controller circuit is decoupled from the implantable medical device.

In Example 33, the method of one or any combination of Examples 30-32 optionally is performed such that the multiplexing includes simplex communication.

In Example 34, the method of one or any combination of Examples 30-32 optionally is performed such that the multiplexing includes duplex communication.

In Example 35, the method of one or any combination of Examples 30-34 optionally comprises: using the first signal to control switching, at a location on the elongate lead body located away from the implantable medical device, to deliver charge from the implantable medical device to a first electrostimulation capacitor located on the lead body away from the implantable medical device; and using the first signal to control switching, at a location on the elongate lead body located away from the implantable medical device, to discharge energy from the electrostimulation capacitor.

In Example 36, the method of one or any combination of Examples 30-35 optionally comprises using the first signal to provide information to control pacing.

In Example 37, the method of one or any combination of Examples 30-36 optionally comprises providing the first signal and the second signal to a second controller circuit located on the lead body away from the implantable medical device; and using at least the first signal and the second controller circuit, controlling a switching on the lead body away from the implantable medical device.

In Example 38, the method of one or any combination of Examples 30-37 optionally is performed such that the multiplexing comprises: communicating a pulse synchronization information from the implantable medical device to the first controller circuit and the second controller circuit using the first signal; and using the pulse synchronization information, controlling switching of first and second switches located on the lead body away from the implantable medical device.

In Example 39, the method of one or any combination of Examples 30-38 optionally comprises switching the first switch and the second switch at a delay specified in the pulse synchronization information.

In Example 40, the method of one or any combination of Examples 30-39 optionally comprises: populating a pacing vector table according to one or more sensed depolarizations; comparing the pacing vector table to a specified pacing vector table; and switching the first switch and the second switch based on the comparison of the pacing vector table and the specified pacing vector table.

In Example 41, the method of one or any combination of Examples 30-40 optionally comprises switching, at the implantable medical device, to control conductivity to a third electrode of the implantable medical device such that a pacing vector extends between at least the first and third electrodes.

This section is an overview of some of the teachings of the present subject matter and is not intended to be an exclusive or exhaustive treatment. Further details are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIG. 3 illustrates a first lead example.

FIG. 4 illustrates a second lead example.

DETAILED DESCRIPTION

Figure 1:
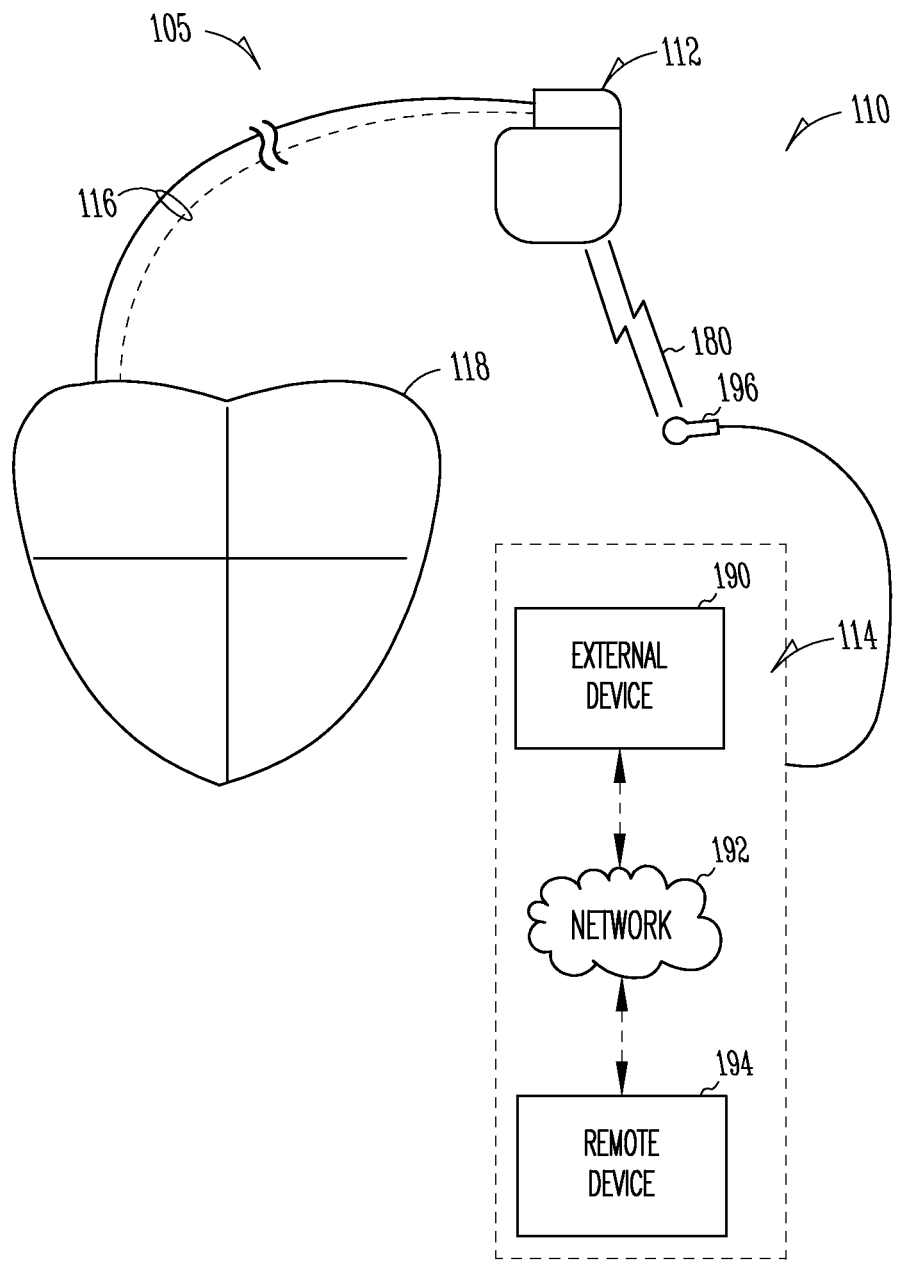
FIG. 1 is an illustration of a cardiac rhythm management system, according to one example.

FIG. 1 is an illustration of an example of a cardiac rhythm management system. In this example, the system 110 generally comprises an implantable subsystem 105 including an implantable medical device 112 and a lead system 116. Some examples include an external subsystem 114. In certain examples, an implantable medical device 112 includes electronic and energy storage components (e.g., a battery and a defibrillation capacitor) located in an implantable case, such as a biocompatible hermetically sealed case. In certain examples, the implantable medical device 112 includes, by way of example, but not by way of limitation, one or more of a pacer, a cardioverter/defibrillator, a cardiac resynchronization therapy (CRT) device, a cardiac remodeling control therapy (RCT) device, a neurostimulator, a drug delivery device or a drug delivery controller circuit, or a biological therapy device.

In certain examples, the implantable medical device 112 is coupled to a lead system 116 that includes multiple leads, which can include at least one electrode for each lead. FIG. 1 shows an illustrative example in which there are two leads. Other examples can include a single lead or more than two leads. In some examples, one or more leads are inserted into or near to a patient's heart 118 or elsewhere in a body. In certain examples, the lead 116 transmits electrical energy ("electrostimulations") to stimulate the heart 118 or one or more additional or other organs. Some examples provide a lead 116 that receives or senses electrical signals from the heart 118 or one or more additional or other organs.

In certain examples, the electrode or lead 116 includes one or more implantable electrodes or sensors, such as for sensing physiological signals (e.g. heart rate), such as from one or more locations within, near, or even some distance away from the heart. The lead 116 can include one or more implantable electrodes for delivering pacing pulses, cardioversion/defibrillation shocks, neurostimulation pulses, or other pulses, such as to one or more locations within, near, or even some distance away from the heart. In some examples, the lead 116 additionally includes a device to deliver a pharmaceutical or other substance. In some examples, the lead 116 includes one or more pacing and sensing leads, which can include at least one electrode configured to be placed in or on a heart 118 for sensing a cardiac electrogram signal or for delivering pacing or cardiac resynchronization pulses. In another example, the lead 116 includes one or more neurostimulation and sensing leads, which can include at least one electrode configured to be placed on a nerve of the autonomic nervous system, such as for sensing one or more neural signals or delivering one or more neurostimulation pulses. In another example, the lead 116 includes one or more pacing and sensing leads and one or more neurostimulation and sensing leads, such as to synchronize or otherwise use neurostimulation with pacing or intrinsic activities of heart 118.

Additionally illustrated are portions of an example of an environment in which an implantable subsystem 105 is used. The inductive, radio frequency (RF), or other telemetry subsystem 114 can be used with the implantable subsystem 105, such as to use information gathered by the implantable subsystem 105. Some examples include a wand 196 or other device that is used to program the implantable medical device 112. Additional examples program the implantable subsystem 105 using additional or other communication devices capable of telemetry.

In some examples, the external subsystem 114 includes a patient management system including a local external device 190 that uses a network 192 to communicate with a remote external device 194. In certain examples, the local external device 190 includes a programmer or repeater that is capable of communicating with the implantable medical device 112. The local external device 190 is generally located within the vicinity of the implantable medical device 112 and communicates with it bidirectionally via telemetry link 180, in certain examples. In some examples, the remote device 194 is in a remote location and communicates with the external device 190 bi-directionally via a network 192, thus allowing a user to monitor or treat a patient from a distant location, such as by using a home computer, personal digital assistant, mobile phone or the like to connect to the remote device 194 over the network 192. In some examples, the external subsystem 114 includes a local external programmer that is configured to communicate with the implantable medical device 112 bi-directionally via the telemetry link 180.

Figure 2:
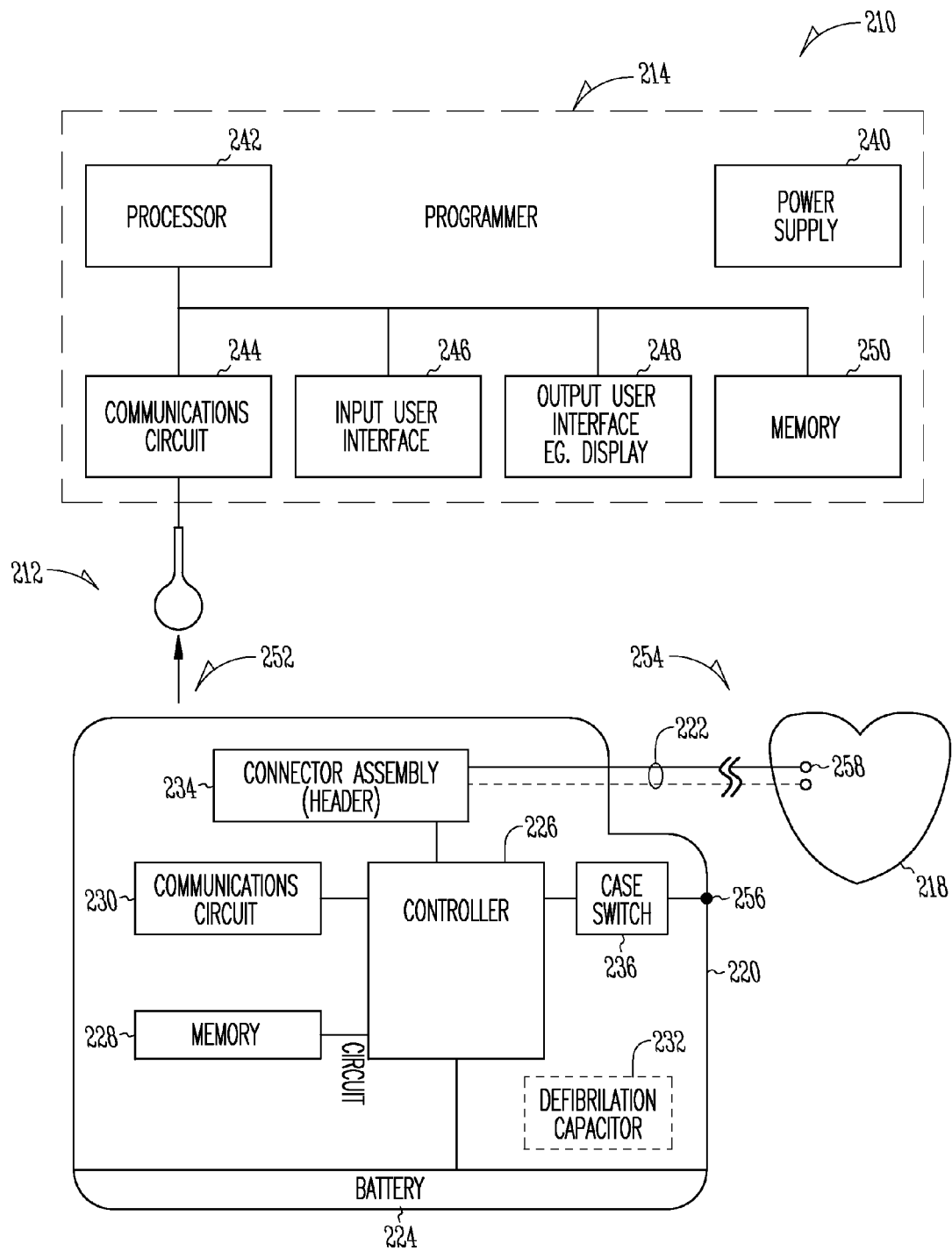
FIG. 2 is an illustration of the cardiac rhythm management system, according to one example.

FIG. 2 is an illustration of a cardiac rhythm management system. In this example, the system 210 includes an implantable medical device 212 and a programmer 214. In an example, the implantable medical device 212 is a programmable microprocessor-based system that includes an implantable case 220, and one, two, or more attachable electrode system lead(s) 222. One of the illustrated leads includes a first conductor in conductive communication with a case switch 236, and a second conductor in conductive communication with a defibrillation capacitor 232. In such a configuration, the defibrillation capacitor 232 can discharge to a grounded implantable case when the case switch 236 is switched to permit such a discharge.

In an example, the implantable case 220 includes components such as a power source such as a battery 224, a controller circuit 226, a memory 228, a communications circuit 230, and an optional defibrillation capacitor 232. Such components are in communication with each other, in certain examples. The controller circuit 226 and memory 228 can be used to control processes conducted by the implantable medical device 212. Some examples provide a case switch 236, such as to switch a case electrode into a "unipolar" pacing configuration, for example. For example, the case switch 236 can switch conductivity between the case electrode and the controller circuit 226 or other node. This can be used, in some examples, to direct a "unipolar" pacing vector conductive path from an electrode 258 located on a distal portion 254 of a lead in the heart 218 to an electrode 256 located on the implantable case 220 via tissue including the heart 218. Although a heart is illustrated in FIG. 2, additional examples can include one or more pacing vectors that go through additional tissues.

The implantable medical device 212 can also include a connector assembly 234 or header that includes an interface for coupling the electrode system lead(s) 222 to the implantable case 220. In an example, the connector assembly 234 includes a lead connector and a connector receptacle for the electrical and mechanical connection of the lead(s) 222 to the implantable case 220.

Certain examples permit multiplexed communication of signals between the implantable medical device and a relatively more distal portion 254 of the lead, such as for multiplexing between (1) communicating information and (2) charging components located in the lead(s) 222. In an example, multiple electrical signals are transmitted sequentially or concurrently, in simplex or duplex, using one or more shared conductors. This can include time division multiplexing, which designates a time slot for the transmission of a particular signal on a shared conductor. This can also use frequency division multiplexing, in which different signals can be communicated concurrently at different frequencies. Packetized communication can also be used, in some examples. Packetized communication signals generally include a mask or header portion, which can include address information such as to help communication circuits 230 and 244 recognize an origin or destination of the packet, and a substance or payload portion, which can includes data such as a program, an energy quantum used to charge a battery or a capacitor, or another type of signal.

In an example, the programmer 214, or another processing device, includes a power supply 240, a processor 242, a communications circuit 244, an input user interface 246, an output user interface 248, and a memory 250 that are in communication with each other. The programmer 214 is capable of communicating with the implantable medical device 212 through a communication link 252. In an example, the communication circuits 244 and 230 provide a radio frequency telemetry link between the programmer 214 and the implantable medical device 212. In another example, the implantable medical device 212 and programmer 214 communicate with each other using mutually coupled inductive coils. The input user interface 246 can include, but is not limited to, a keyboard, a mouse, a light pen, or a touch screen. The output user interface 248 can include, but is not limited to, a printer or a display. In an example, the programmer 214 is capable of programming the implantable medical device 212, such as including the configuration of the electrode system, and is capable of collecting sensor or other data from the implantable medical device.

Figure 5:
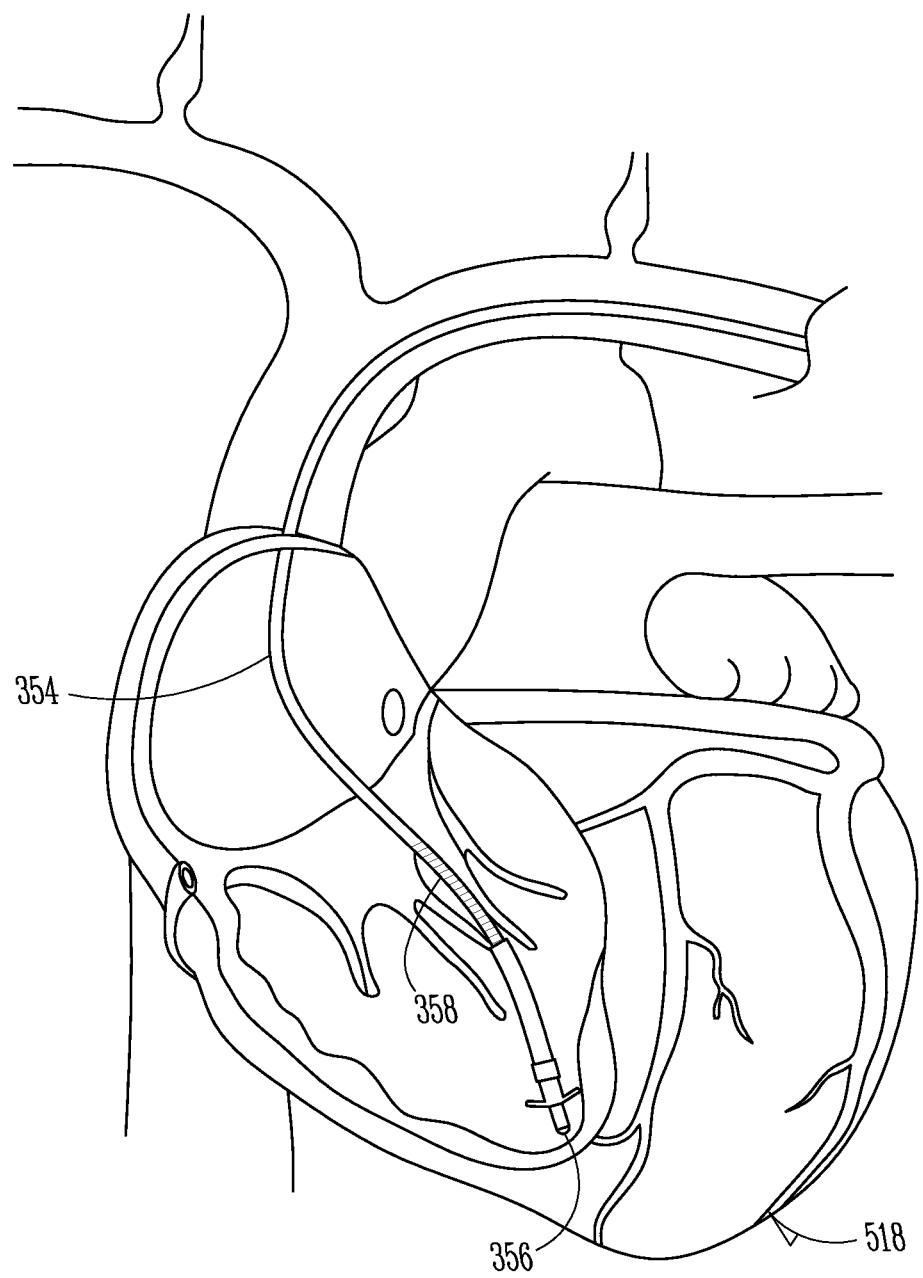
FIG. 5 illustrates one example of the lead shown in FIG. 3.
Figure 6:
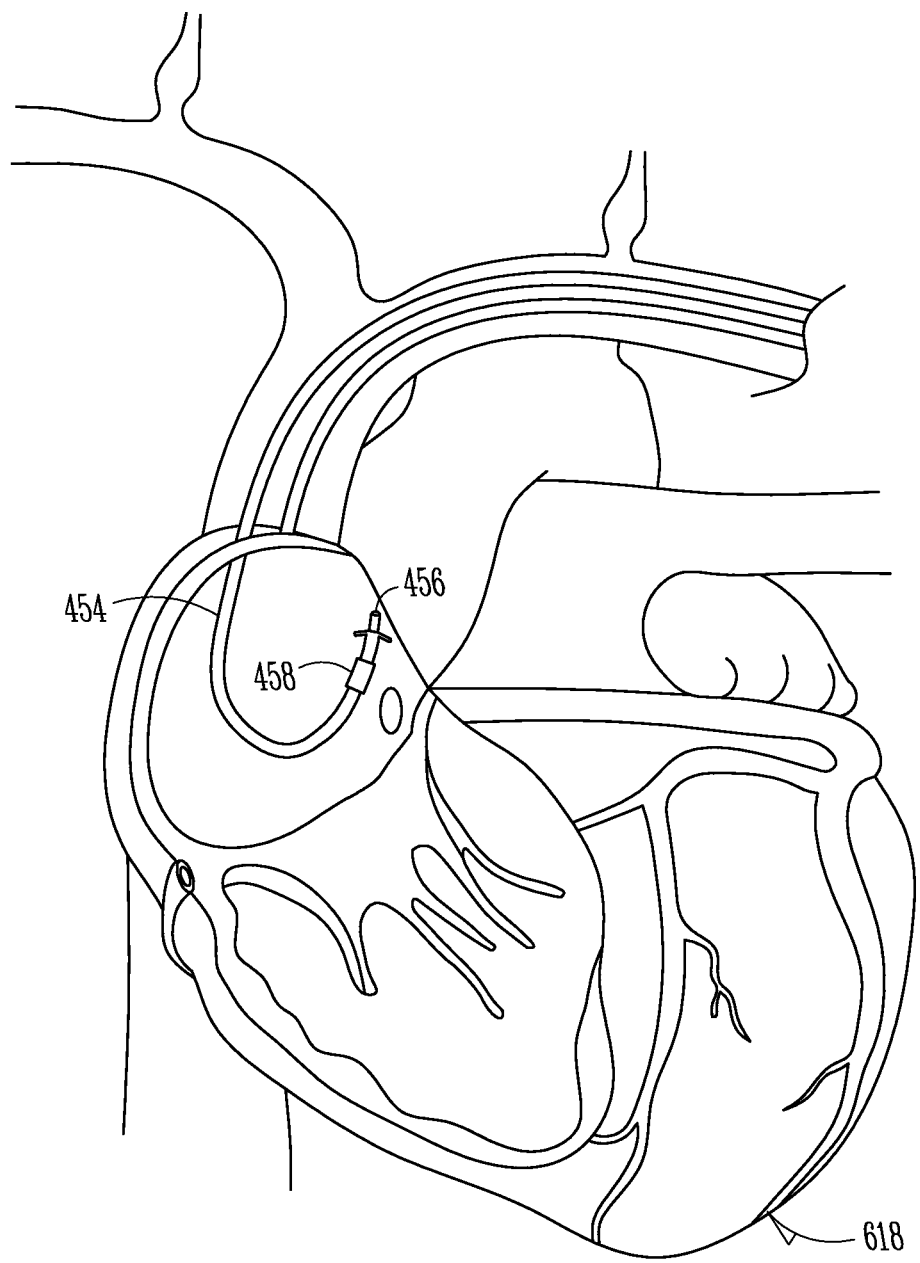
FIG. 6 illustrates one example of the lead shown in FIG. 4.

FIG. 3 illustrates an example of a first lead 354, and FIG. 4 illustrates an example of a second lead 454, although not drawn to scale. The first lead 354 shown in FIG. 3 includes a tip electrode 356 and a first coil electrode 358. The first lead 354 may be used, for example, in an implantable cardioverter defibrillator. The second lead 454 shown in FIG. 4 includes a tip electrode 456 and a first ring electrode 458. The second lead 454 may be used, for example, in an implantable pacer. FIG. 5 illustrates an example of an arrangement of the first lead 354 in a heart 518 and FIG. 6 illustrates an example of an arrangement of the second lead 454 in a heart 618; additional electrode configurations are possible.

In certain examples, electrical energy can be delivered to a patient between two or more electrodes on the same lead, between two or more electrodes on different leads, or between a conductive surface on the pulse generator (e.g., located on a implantable case or header) and one or more electrodes on one or more leads. The leads and electrodes are capable of being placed in a number of areas or locations other than those listed herein expressly. The electrical energy can include an electrostimulation energy (e.g., a pacing, anti-tachyarrhythmia pacing (ATP) or CRT pulse), a defibrillation shock, or a test energy (e.g., for measuring a tissue impedance or the like).

The electrode system can also be capable of sensing intracardiac electrical activity. In some examples, if leads are already in place for the purpose of stimulating a heart, it is desirable to provide the lead with one or more additional sensing capabilities such as, but not limited to, biochemical sensing capabilities. The present devices and methods can also address difficulties involved with including additional sensors on the lead and sensing other than intracardiac electrical activity.

For example, sensors and supporting electronics are capable of being fabricated using micro-electromechanical systems (MEMS) or using other semiconductor technology. A MEMS device can include micro-circuitry on a substrate. Semiconductor substrates are possible, as are other substrates. MEMS chips can include mechanical or electromechanical devices, including a sensor. These chips can be built in large quantities at low cost, making the MEMS device cost-effective, such as for being incorporated into an intravascular lead In an example, one or more sensor(s) or supporting electronics are incorporated into an implantable medical device lead. A MEMS device on an implantable medical device lead can be used to combine electrical pacing or sensing by an implantable medical device lead with other sensing capabilities (e.g., blood pressure, blood flow, blood chemistry, or the like). The sensor(s) associated with the MEMS device(s) is capable of being positioned anywhere along the lead as desired for the application, such as at a distal portion of the lead, for example. Multiplexed communications can be used to incorporate the MEMS device on a lead without requiring any additional connections between the lead and the implantable medical device to which the lead is coupled. As a result, an implantable medical device can be provided with extra sensing capability without deviating from the International Standard (IS) standard for an implantable medical device header to which the lead is coupled.

Figure 7:
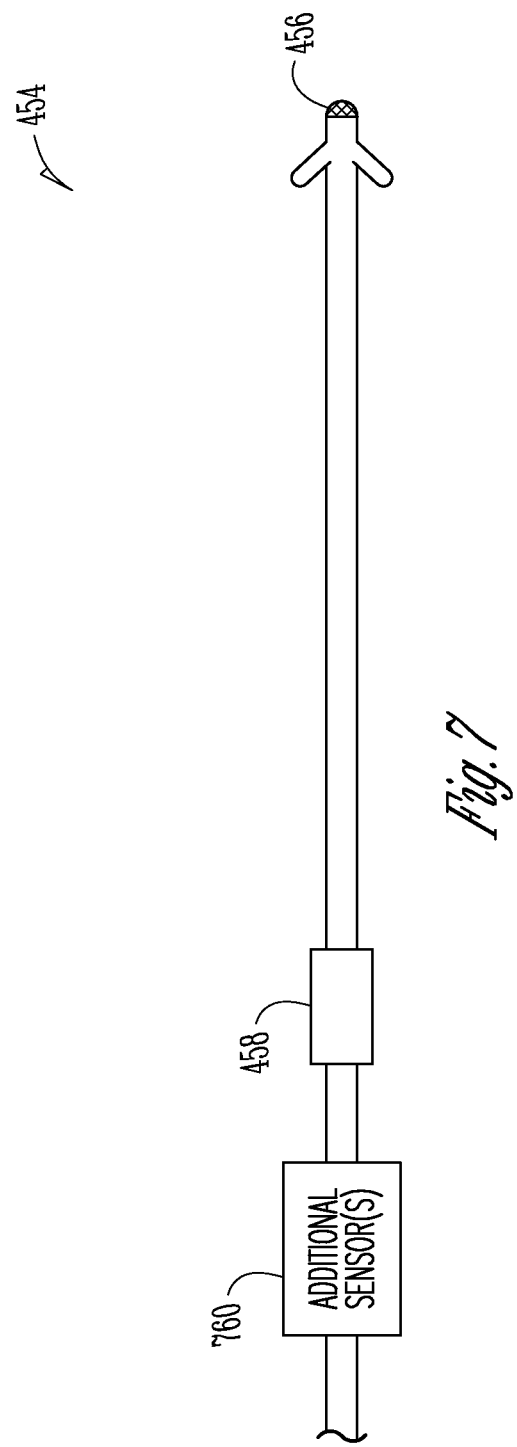
FIG. 7 illustrates one example wherein additional sensor(s) are added to a standard lead.
Figure 8:
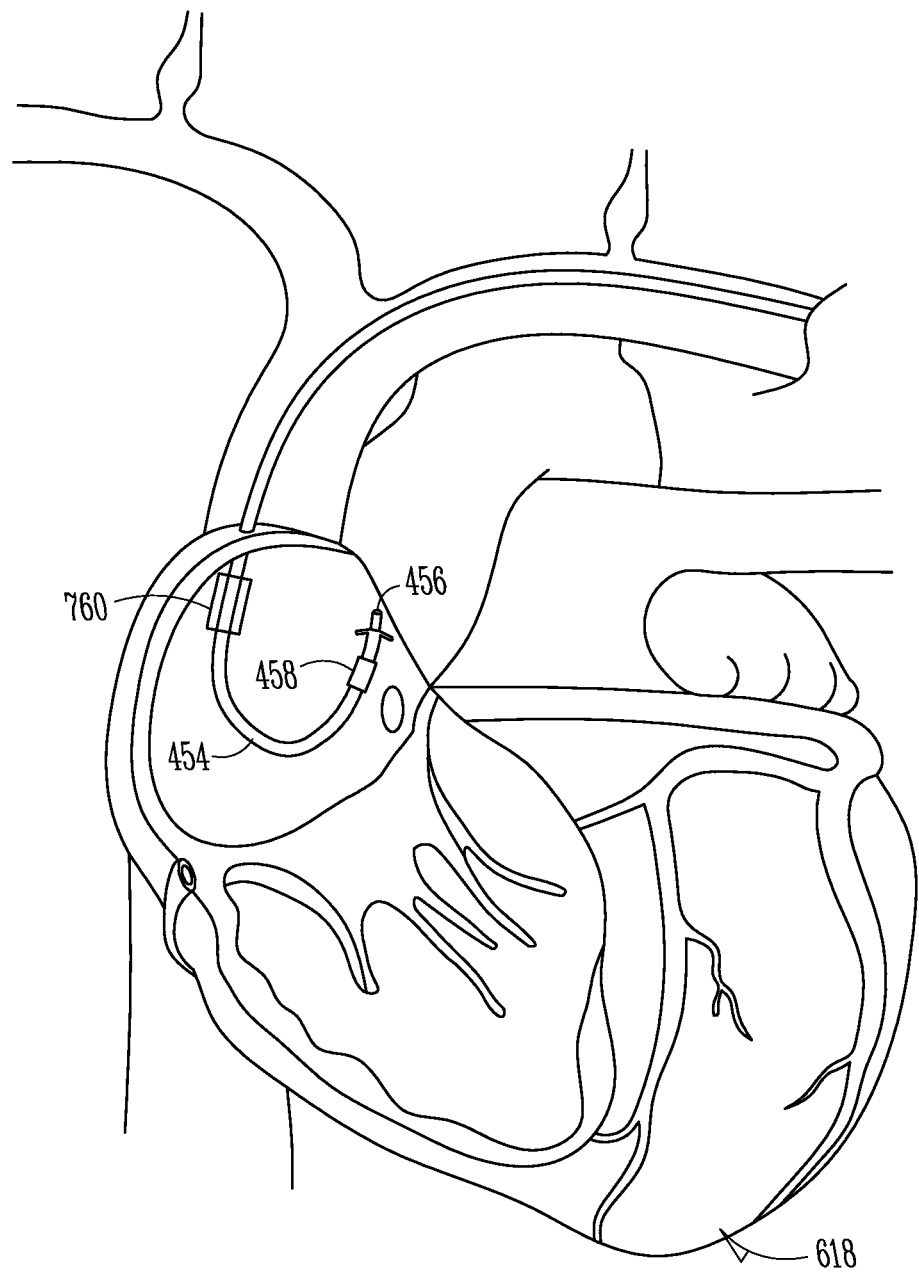
FIG. 8 illustrates one example of the lead shown in FIG. 7.

FIG. 7 illustrates an example in which one or more additional sensor(s) are added to a standard lead. In this example, sensor(s) 760 are included in addition to the tip electrode 456 and the ring electrode 458 for the second lead 454 that was previously shown in FIG. 4. In an example, the additional sensor(s) 760 can include a MEMS device. FIG. 8 illustrates an example of an arrangement of the lead shown in FIG. 7. Additional leads, lead arrangement, and electrode configurations are also possible. In an example, the additional sensor(s) include one or more biochemical sensors. In certain examples, the additional sensor(s) sense one or more of: oxygen, carbon dioxide, catecholamine, pressure, local acceleration, or temperature. Other sensors or like devices not recited herein expressly can be included.

Figure 9:
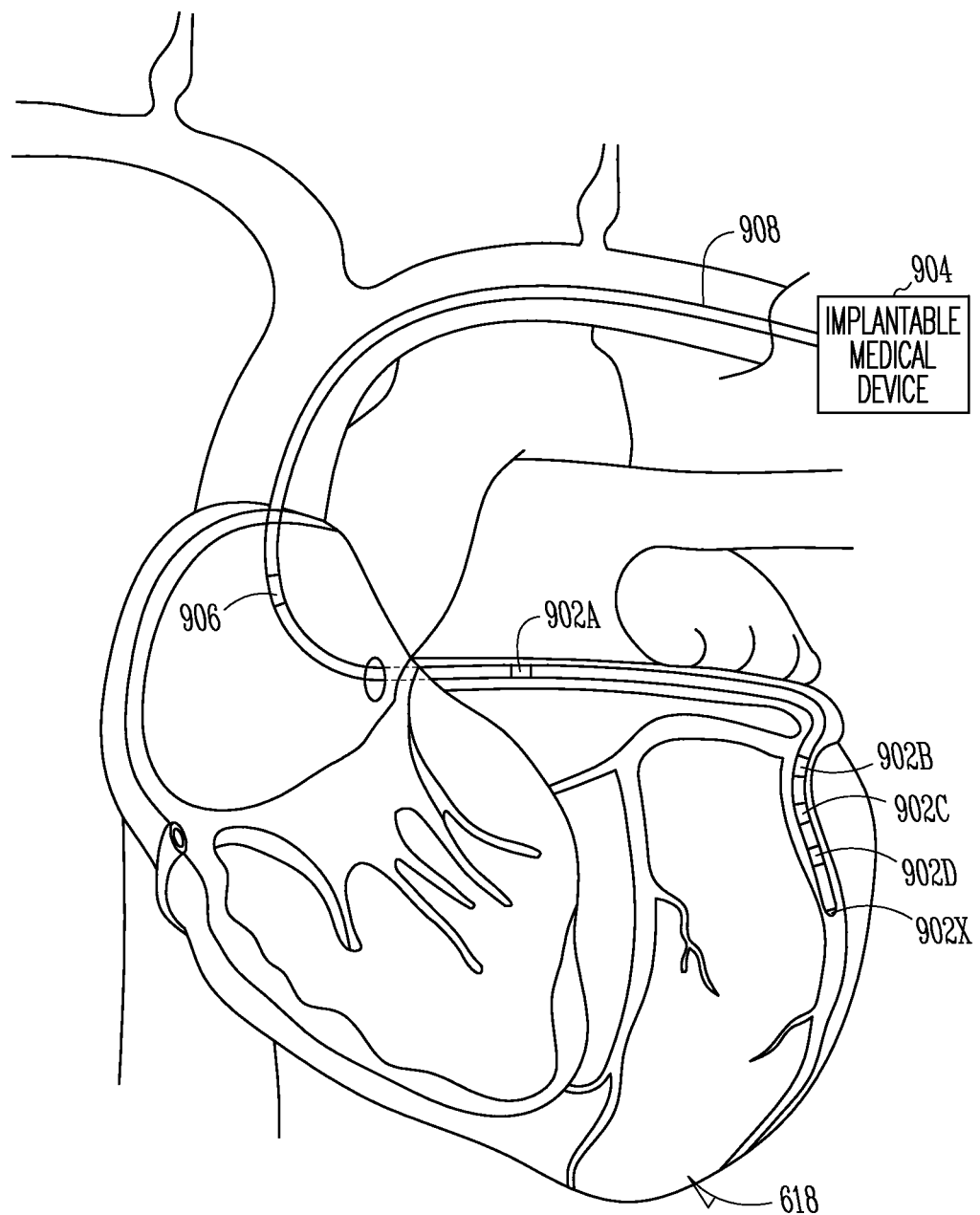
FIG. 9 illustrates a lead in a heart, according to one example.

FIG. 9 illustrates an example of a lead in a heart. The example of FIG. 9 includes an arbitrary number of loads 902A through 902X, which are in multiplexed communication with the implantable medical device 904. Additionally illustrated is a right atrial pacing electrode 906 that is in multiplexed communications with an implantable medical device 904. In some examples, the pacing electrode 906 and the loads 902A through 902X communicate with the implantable medical device 904 over a shared conductor.

In an example, the loads 902A through 902X can individually be switched into communication with electronics disposed in lead body 908. In some examples, an electrode, such as electrode 902A, is provided with electrostimulation energy such as to evoke depolarization of cardiac or other tissue. If a resulting depolarization is detected, a memory location in one of the electronics disposed in the lead 908 or the implantable medical device 904 can be updated to reflect that the electrode 902A has "captured" the tissue. If a resulting depolarization is not detected, a memory location can be updated accordingly. In an example, the electrodes 902A through 902X can each be subjected to such a capture test that can also be carried out at different electrostimulation energies, such as to ascertain how much energy is needed for such capture. The stored information then can be used to selectively switch on only one or more of those electrodes out of 902A through 902X that have captured tissue, thereby directing a selected electrostimulation energy to corresponding locations that are more receptive to the electrostimulation pulse. This can allow for an electrostimulation pulse(s) of lower energy, which can conserve battery life of a battery used to provide energy for the electrostimulation pulse. Lower power consumption allows for smaller implantable medical devices, such as implantable medical device 904. Smaller implantable medical devices are easier to implant and are more comfortable to live with.

Figure 10A:
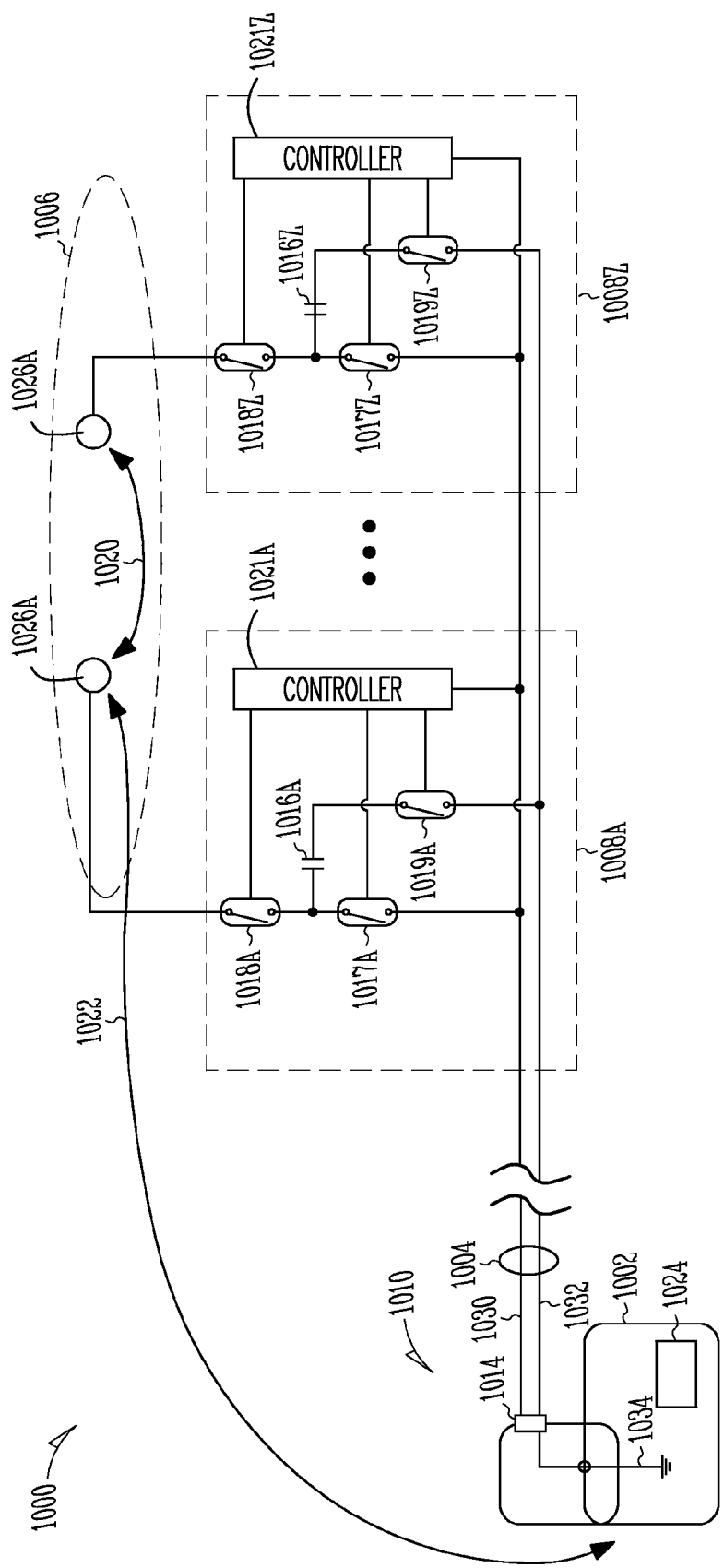
FIG. 10A illustrates an example of a system with electrostimulation capacitors disposed in a lead.

FIG. 10A illustrates an example of a diagram that shows an implantable medical device with a multi-electrode lead. FIG. 10A shows an implantable pulse delivery system 1000 that includes an implantable medical device 1002 that can include a case that can be implanted under the skin. A battery 1024 powers the system 1000. The implantable medical device 1002 can include a defibrillation capacitor or other components that are too large to be positioned in the patient's vasculature or heart chamber.

A lead 1004 is coupled to the implantable medical device 1002. The lead is shown including multiple conductors 1030, 1032. In other examples, multiple leads can be included. The illustration also shows a tissue portion 1006, such as a heart, in some examples. Some examples include an arbitrary number of loads 1008A through 1008Z that are located near or abutting a corresponding specific tissue portion. For example, tissue portion 1006 includes a first specific tissue location 1026A and a second specific tissue location 1026Z. A load can include an electrode, a sensor, or another type of load. Examples of sensors used in certain examples of system 1000 can include one or more sensors to sense a biochemical, oxygen, carbon dioxide, catecholamine, temperature, pressure, an intrinsic electrical cardiac signal, or the like.

In certain examples, the tissue portions include any of the atria or ventricles, or vasculature associated with the heart, such as the coronary sinus or the great cardiac vein, for example. In some examples, the lead 1004 is disposed in the coronary sinus, with the loads 1008A through 1008Z disposed at various different locations along the coronary sinus. Some examples locate loads 1008A through 1008Z along a lead 1004 that is disposed in the right atrium and right ventricle, with loads 1008A through 1008Z located along lead 1004 such that some are located in the right atrium and others are located in the right ventricle. Other configurations are possible.

In certain examples, the lead 1004 includes an elongate lead body. In some examples, the elongate lead body includes a proximal portion 1010 and a distal portion 1012 located between proximal and distal ends. In certain examples, the lead 1004 includes a coupler 1014, located at the proximal portion 1010 of the lead body, such as at the proximal end of the lead body. The coupler 1014 is configured to be coupled to the implantable medical device 1002, such as by using a connector that mates with a header of the implantable medical device 1002. In an example, the coupler 1014 is suitable for providing a connection, between a first conductor and a second conductor, which is sealed from body fluid.

In an example, a conductor 1030 extends from the coupler 1014 at the proximal portion 1010 of the lead body to a distal portion of the lead body. In an example, the conductor can be coupled to at least a first load 1008A located at the distal portion of the lead body. In some examples, a first electrostimulation capacitor 1016A is located at the distal portion of the lead body. The first electrostimulation capacitor 1016A has a capacitance value that is large enough to store an electrostimulation energy that is large enough to perform electrostimulation of tissue. In some examples, the electrostimulation capacitor 1016A has a capacitance value that is large enough to store an electrostimulation energy that is large enough to evoke contraction of myocardial tissue. Some examples use a conductor 1030 disposed in the lead body 1004 (e.g., between the proximal end coupler and the electrostimulation energy storage capacitor) that includes a conductor gauge size that is smaller than a gauge size that would otherwise be needed to deliver the electrostimulation energy at a specified voltage from an electrostimulation storage capacitor in the implantable medical device through the proximal coupler and conductor to the electrode at the distal portion of the lead and the tissue (e.g., without using the electrostimulation capacitor to store the electrostimulation energy at the distal portion of the lead body at the specified voltage). Some examples can carry pulses at 70 volts or higher.

Some examples include a first switch 1017A located at the distal portion of the lead body and coupled between the conductor and the electrostimulation capacitor, and a second switch 1018A located at the distal portion of the lead body and coupled between the electrostimulation capacitor and the first electrode. The first switch 1017A can be configured to selectively couple the first electrostimulation capacitor 1016A to the conductor during a charging state. The second switch 1018A can be configured to selectively couple the electrostimulation capacitor 1016A to the first electrode 1008A during a stimulating state. Some examples include a third switch 1019A which selectively provides a ground for the electrostimulation capacitor 1016A. In an example a specified number of electrostimulation capacitors are used, such as a desired number of electrostimulation capacitors 1016A through 1016Z.

One or more controller circuits 1021A through 1021Z can be located in the lead 1004 and coupled to the conductor 1030. These controller circuits 1021A through 1021Z can be configured to communicate with the implantable medical device 1002, such as by using multiplexed communication. In an example, the multiplexer circuit in the implantable medical device 1002 can be configured to multiplex over the conductor 1030 at least a first signal and a second signal. The first signal can be a charging signal intended to deliver a quantum of energy to charge a capacitor such as the capacitor 1016A to a desired level, such as for electrostimulating tissue 1006, in some examples. The first signal can also include encoded information, such as data or a program, for example. Examples of programs contemplated include pulse delivery programs such as ventricular synchronization programs, pacing programs, sensing programs, communications programs that control how the implantable medical device 1002 communications with the one more loads 1008A through 1008Z, or other programs. In certain examples, a controller circuit 1021A through 1021Z includes a timer circuit, and the pulse delivery program includes a specified delay used by the timer to control a switch, for example, that conductively couples a first electrode to the electrostimulation capacitor after the specified delay.

The first or second signals, in some examples, include addressing information, such as to identify a destination to where the implantable medical device 1002 is directing a signal, or vice-versa. In an example, the first controller circuit is configured to control the first switch 1018A based at least on the first signal.

Due in part to the multiplexing capability that can carry charging and information signals, some examples include a lead body that includes one conductor extending from the proximal portion 1010 of the lead 1030 to the distal portion 1012 of the lead 1030 for charging electrostimulation capacitors 1016A through 1016Z and for carrying multiplexed information. A second conductor 1032 can be included for grounding components included in loads 1008A through 1008Z to ground 1034. Ground 1034 is connected to an implantable case of the implantable medical device 1002 in some examples. This connection can be selectively switched on and off in some examples. In examples where the ground 1034 is not grounded to an implantable case of the implantable medical device 1002, a ground for conductor 1032 is provided in the implantable medical device using electronics, such as battery 1024. There may be more than these conductors extending from the proximal portion 1010 to the distal portion 1012 of the lead 1030. The components disposed in loads 1008A through 1008Z are capable of being fabricated using micro-electromechanical systems (MEMS) or using other semiconductor technology.

In certain examples, the system 1000 includes a lead that includes a controller circuit, located at the distal portion of the lead body. The controller circuit can be coupled to the conductor and configured to use the conductor, such as to multiplex: (1) receiving a communication signal from the implantable medical device via the conductor and (2) charging of the electrostimulation capacitor or other capacitor located on the lead away from the implantable medical device via the conductor.

FIG. 10A illustrates an example of a first electricity path vector 1020 and a second electricity path vector 1022. During electrostimulation by the system 1000, electricity can travel along one of these vectors. The system 1000, in certain examples, is capable of monitoring intrinsic electrical signals in the tissue 1006, such as for determining the need for or the efficacy of electrostimulation therapy. In some examples, the implantable medical device 1002 receives one or more communication signals including information relating to tissue 1006, collected by one or more sensors, and analyzes the data. The analysis, in certain examples, can occur in components located in the lead away from the implantable medical device 1002. Examples of such lead-based components can include controllers, electrodes, and other components located near the tissue 1006 and discussed herein. If the analysis indicates better performance of one vector over another, that better-performing vector can be selected to provide subsequent therapy, such as until another optional analysis indicates otherwise. The systems and methods are not limited to feedback systems based only on data collected by system 1000. Instead, the systems and methods can use one or more other tools to indicate or suggest alternative therapies to implantable medical device 1002 or one or more controllers disposed in lead 1004.

Figure 10B:
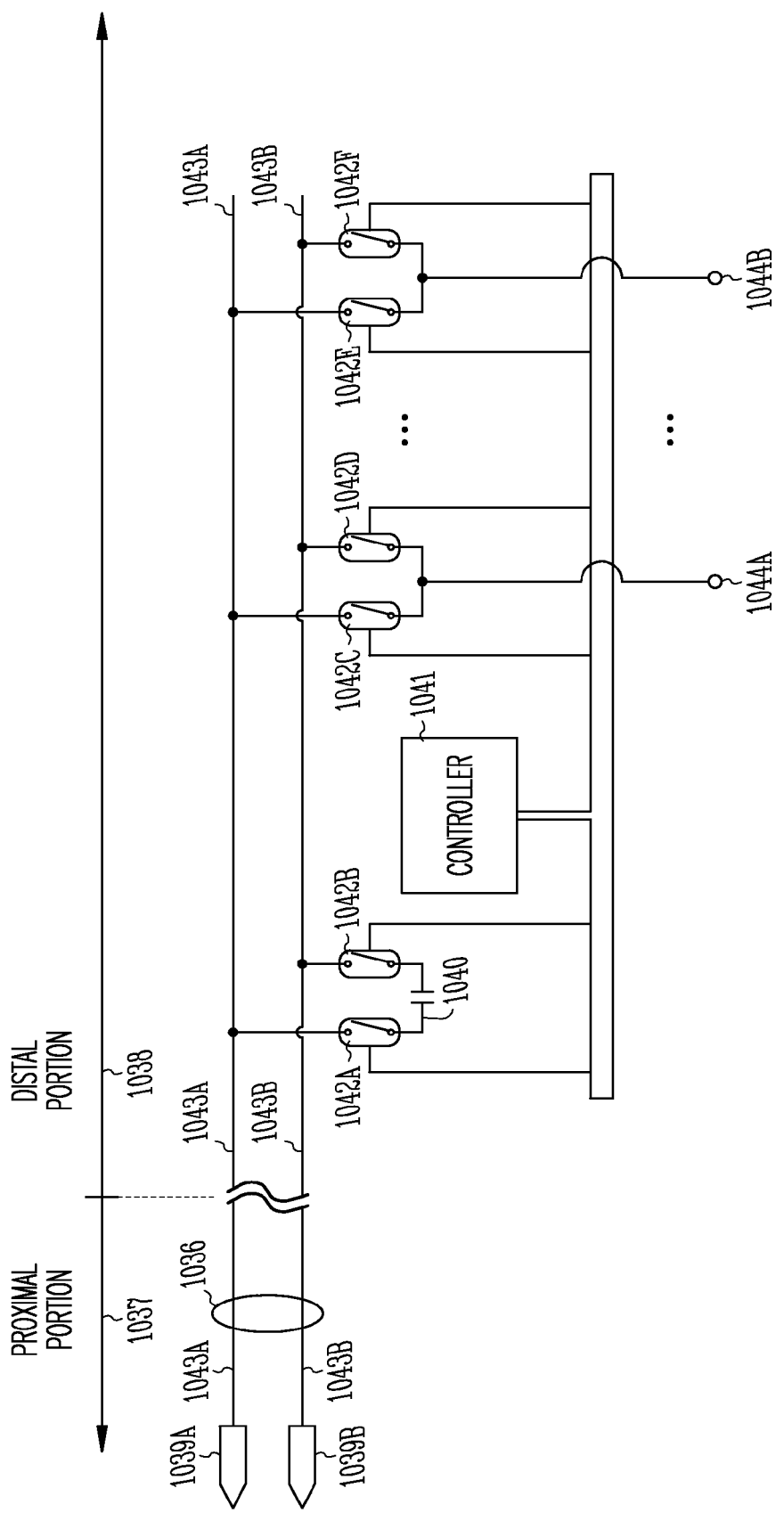
FIG. 10B illustrates an example of a lead in which an electrostimulation capacitor located at a distal portion of the lead can be shared between multiple electrodes.

FIG. 10B is a diagram illustrating an example of a lead 1036. In this example, a proximal portion 1037 includes connectors 1039A-B, which can be configured to plug into mating receptacles of an implantable medical device 1002. A distal portion 1038 can include an electrostimulation capacitor 1040 for storing an electrostimulation energy. The distal portion 1038 of the lead 1036 can also include at least one controller 1041 circuit, such as to control operation of switches 1042A-F. The IMD 1002 can also include series switches, such as can be configured for connecting or isolating the IMD 1002 from the conductors 1043A-B of the lead 1036. Each electrode 1044 can include a switch to selectively couple that electrode to one of the conductors 1043A-B. In the example of FIG. 10B, the electrode 1044A can be selectively coupled to the conductor 1043A by the switch 1042C, or to the conductor 1043B by the switch 1042D. Similarly, the electrode 1044B can be selectively coupled to the conductor 1043A by the switch 1042E, or to the conductor 1043B by the switch 1042F. Other electrodes 1044 can similarly be included, together with corresponding switches to selectively couple such electrodes to one of the conductors 1043A-B.

In the example of FIG. 10B, the electrostimulation capacitor 1040 can service two or more electrodes 1044, such as can be located on the distal portion of the lead 1036. The switches 1042A-B can be turned on (along with series switches in the IMD 1002 for connecting to the conductors 1043A-B) to charge the electrostimulation capacitor 1040 between deliveries of energy from the electrostimulation capacitor 1040 to the tissue via the electrodes 1044. To hold the electrostimulation energy upon the electrostimulation capacitor 1040, the switches 1042A-B (and series switches in the IMD 1002) are turned off. To deliver electrostimulation energy to the electrode 1044A, the switches 1042A, 1042B, and 1042C are turned on. For unipolar electrostimulation, an electrode at the IMD 1002 can be used for the return path, such as by turning on the series switch in the IMD 1002 to couple such electrode at the IMD 1002 to the conductor 1043B. For bipolar electrostimulation, the electrode 1044B can be coupled to the conductor 1043B by turning on the switch 1042F. After delivery of the electrostimulation to the tissue, the electrostimulation capacitor 1040 can be recharged (such as described above), or it can be similarly used to deliver an electrostimulation energy to the tissue via another electrode 1044, such as in a manner analogous to that described with respect to electrode 1044A. For example, electrostimulation energy can be delivered via the electrode 1044B by turning on the switches 1042A, 1042B, and 1042E and (e.g., for bipolar stimulation), the return electrode 1044A can be coupled to the conductor 1043B by turning on the switch 1042D.

Figure 10C:
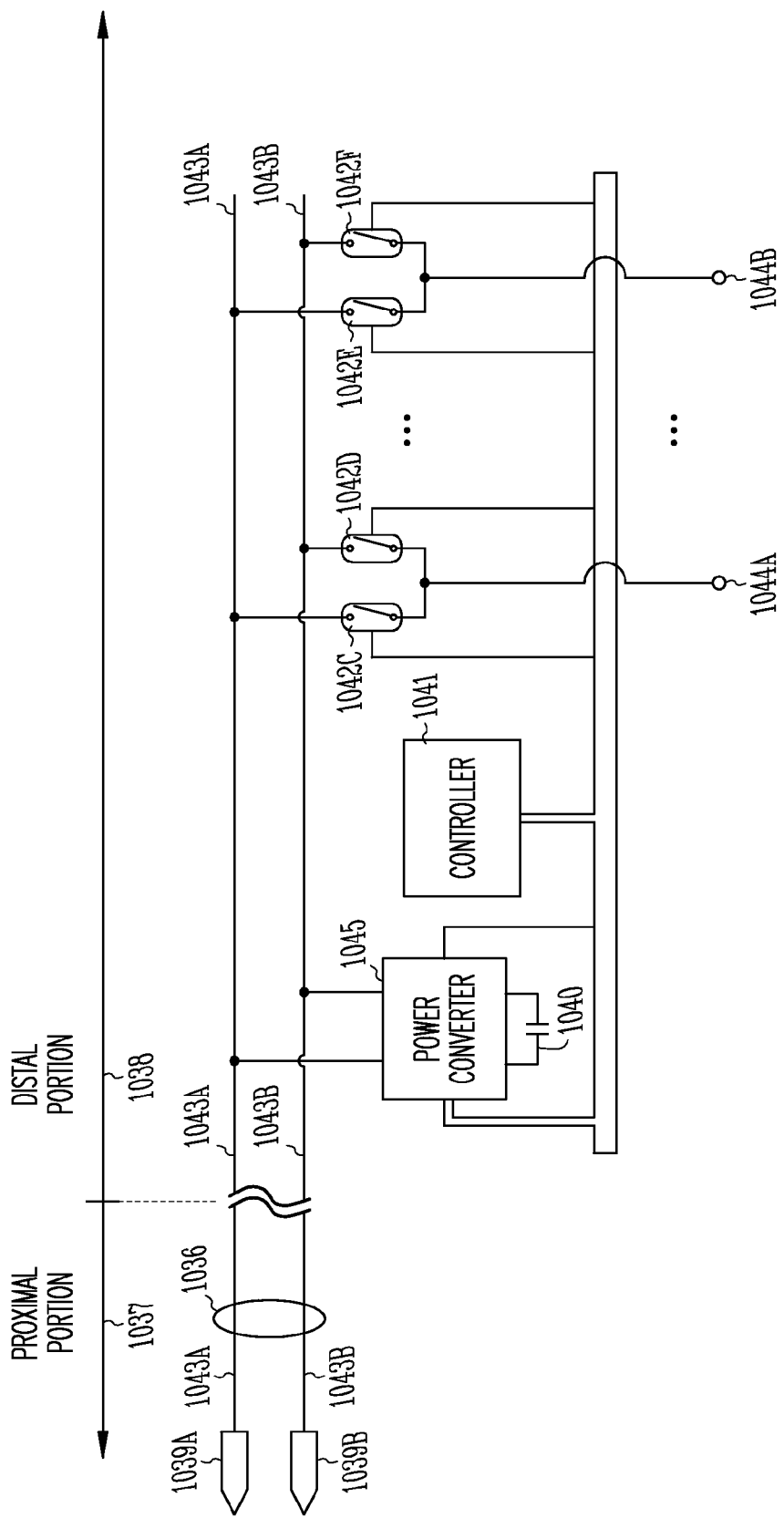
FIG. 10C is a diagram illustrating an example including a power converter circuit located at the distal portion of the lead.

FIG. 10C is a diagram illustrating an example in which the switches 1042A-B for the electrostimulation storage capacitor 1040 are replaced or augmented by a power converter circuit 1045 located at the distal portion 1038 of the lead 1036. In certain examples, the power converter circuit 1045 is a continuous-time circuit, such as a linear regulator. In certain examples, the power converter circuit 1045 is a switched mode circuit, such as a switched-capacitor circuit or a switched inductor circuit (e.g., buck, boost, buck-boost, flyback, or the like). Switching can be controlled by one or more signals provided by the controller 1041. In certain examples, the power converter circuit 1045 can operate to transform the voltage across the conductors 1043A-B to a desired larger or smaller voltage stored across the electrostimulation capacitor 1040, such as may be desired for electrostimulation. In certain examples, the power converter circuit 1045 can operate to transform the voltage stored across the electrostimulation capacitor 1040 to a desired larger or smaller voltage across the conductors 1043A-B, such as may be desired for electrostimulation.

Figure 10D:
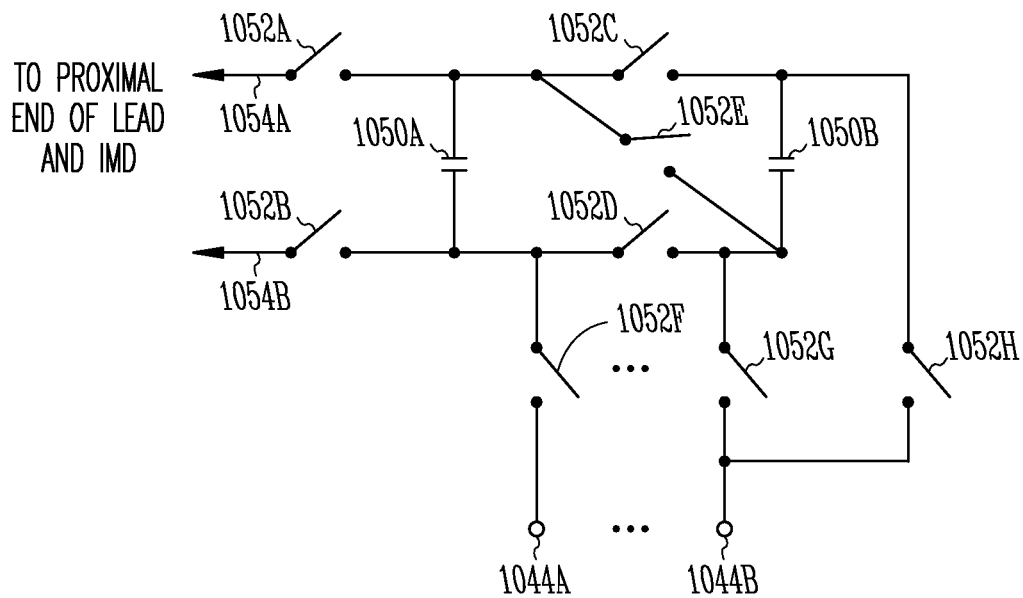
FIG. 10D is a diagram illustrating an example in which, if desired, the distal portion of the lead can be completely decoupled from the implantable medical device during delivery of the electrostimulation energy.

FIG. 10D is a diagram illustrating an example in which, if desired, the distal portion of the lead can be completely decoupled from the implantable medical device 1002 during delivery of the electrostimulation energy. This example includes at least two capacitors 1050A-B, which can be charged by closing switches 1052A, 1052B, 1052C, and 1052D, while the switches 1052E, 1052F, 1052G, and 1052H remain open. After charging, the switches 1052A-H can remain open to hold the stored charge on the capacitors 1050A-B. Then, to deliver electrostimulation energy to tissue, switches 1052E, 1052H, and 1052F can be closed, while the switches 1052A, 1052B, 1052C, 1052G remain open. In such an example in which the distal portion of the lead can be completely decoupled from the implantable medical device 1002 during delivery of the electrostimulation energy, the conductors 1054A-B need only be sized to handle the current density during the longer charging intervals between electrostimulations, rather than to handle the larger current density during the shorter electrostimulation delivery intervals. This can help reduce the lead diameter, making the lead easier to position, such as within a narrow, tortuous vessel, and can help reduce the amount of the vessel that is being occluded by the lead. The lower current density may also permit use of the body itself as a conductor, thereby even allowing the possibility of a single conductor extending between the distal portion of the lead and the proximal portion of the lead.

Figure 11:
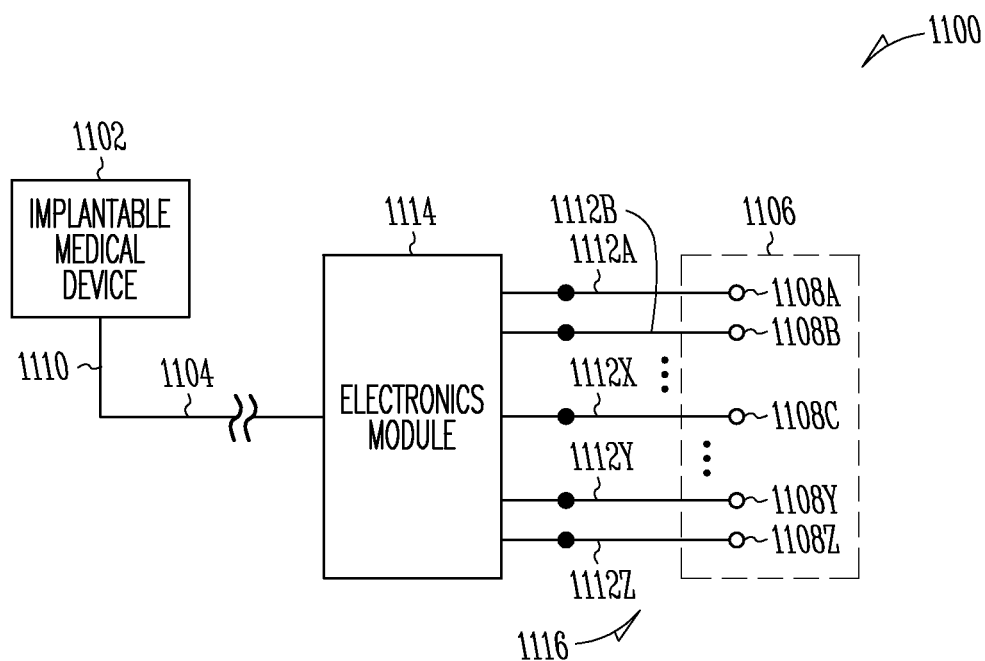
FIG. 11 illustrates a diagram of an implantable medical device with a multi-electrode lead, according to one example.

FIG. 11 illustrates a diagram of an example of electronics in a lead. In this example, an implantable pulse delivery system 1100 includes an implantable medical device 1102 and a lead 1104 coupled thereto. The lead 1104 includes a proximal portion 1110 and a distal portion 1116 between respective proximal and distal ends. An electronics module 1114 that includes electronics is coupled to the implantable medical device 1102, such as at a location on the lead 1104 that is away from the implantable medical device 1102, such as at the distal portion 1116 of the lead 1104. Leads 1112A through 1112Z are connected to the electronics module 1114.

The illustration shows a tissue portion 1106, which can include at least a portion of a heart. Some examples provide electrodes that can be coupled to specific tissue portions to provide one or more loads 1108A through 1108Z. Examples of specific tissue portions can include any of the atria or ventricles, as well as vasculature associated with the heart, such as the coronary sinus, the great cardiac vein, or the like. Certain examples also include a conductor, extending from the proximal portion 1110 of the lead 1104 to the electronics module 1114.

Figure 12:
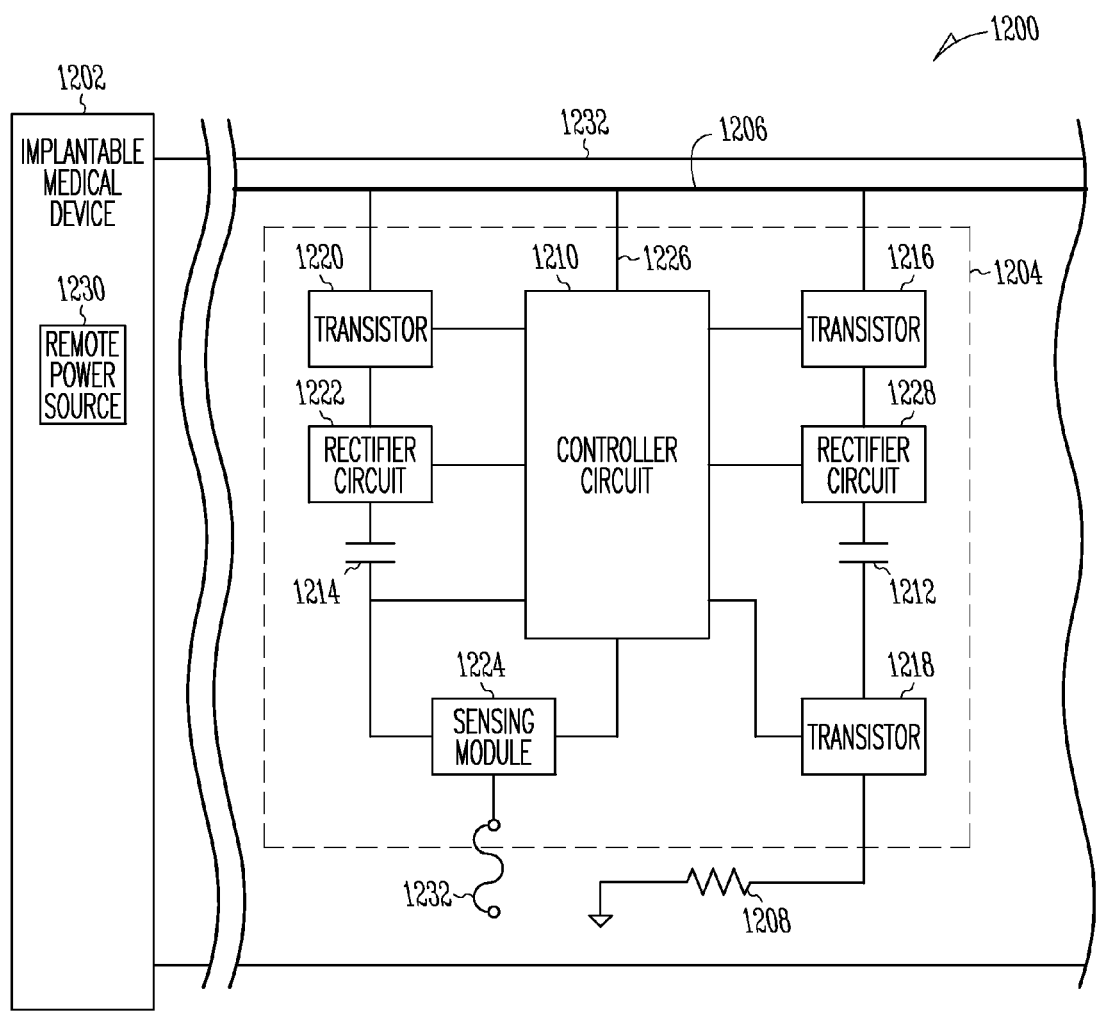
FIG. 12 illustrates a diagram of an implantable medical device and a lead, which branches into additional leads, according to one example.

FIG. 12 illustrates a diagram of an example of electronics in a lead. In certain examples, the system 1200 includes an implantable medical device 1202 that houses a remote power source 1230. A lead body 1232 is coupled to the implantable medical device 1202. In certain examples, the implantable medical device 1202 is connected to one or multiple lead nodes 1204 via a conductor 1206. The conductor includes signals that include charging energy for capacitors 1214 and 1212, in some examples, and in additional examples also carries communications signals. In some examples, these signals are carried by conductor 1206 concurrently. Lead node 1204 is located proximal tissue 1208, in certain examples. Tissue 1208 is tissue targeted for therapeutic treatment. This can be a heart or another tissue.

Certain examples use coordinated timing to operate system 1200. In some examples, the implantable medical device 1202 transmits energy to one or more lead nodes 1204. In some examples, the implantable medical device 1202 relays instructions to and receives information from the lead node 1204. In some examples, a signal includes information from multiple lead nodes.

In certain examples, the implantable medical device 1202 transmits a charging signal during portions of a signal communication cycle, and transmits one or more communications signals during a time period when a charge signal is not being communicated. During these time periods, it is also possible to communication multiple signals concurrently. In some examples, charge signals include high voltage alternating current (AC) signals. Some signals include direct current (DC) signals. Communication portions of the timing cycle can include low voltage encoded data. Both energy transmission and communication can take place through the same transmission conductor 1206, concurrently or sequentially. Multiplexing is possible, as discussed herein.

Lead node 1204 includes various components that are illustrated diagrammatically in FIG. 12. This configuration is one of multiple possible configurations. The illustrated lead node includes a controller circuit 1210, capacitors 1212, 1214, transistors 1216, 1218 and 1220, rectifier circuits 1222, 1228, as well as sensing module(s) 1224, which includes a tissue interface 1232 and supporting circuitry.

Through coordinated timing, different conductive paths lead to conductor 1206. During communication periods transistors 1216 and 1220 maintain an open circuit with conductor 1206, and low voltage communication takes place between conductor 1206 and controller circuit 1210 between line 1226. During capacitor charging periods transistors 1216, 1220 maintain a closed connection with conductor 1206 allowing high voltage charge transfer to take place, resulting in the charging of capacitors 1212 and 1214. In some examples in which this charge transfer takes place using AC power, rectifiers 1222, 1228 are implemented. These rectifiers can also be used in instances where a voltage step is desired. Capacitor 1214 provides power to controller circuit 1210, while capacitor 1216 stores charge to be delivered as therapy to tissue 1208. To deliver therapeutic shock, controller circuit transistor 1210 closes the circuit between capacitor 1212 and tissue 1208. In certain examples, the sensor module 1224 is coupled to the controller circuit 1210 and the powering capacitor 1214, with switches 1220, 1216 and 1218 configured to selectively couple the powering capacitor to the sensor during a sensor powering state for powering the sensor circuit. This sensor powering state, in certain examples, includes transmitting charge that originated from power source 1230 and that was stored in capacitor 1214 to sensor module 1224.

In some examples, a controller circuit 1210 is configured to control a first switch 1218 to selectively decouple the electrostimulation capacitor 1212 from the first electrode 1204 concurrent to selectively coupling the sensor 1224 to the first electrode.

The following elements allow for slower charge transfer rates between the implantable medical device 1210 and the lead node 1204, which translates to lower current desired in the conductor 1206. The capacity within the controller circuit 1210 to communicate individually with the implantable medical device 1210 as well as other controller circuits 1210 housed in other lead body 1232 accommodates the functioning of multiple electrodes, in some examples. These electrodes are controlled through a single cable that has a reduced diameter over existing designs.

The present lead node includes an electrode and a sensor. Some configurations contain one or the other. Some examples include a lead 1232 that includes a mix of nodes.

Figure 13:
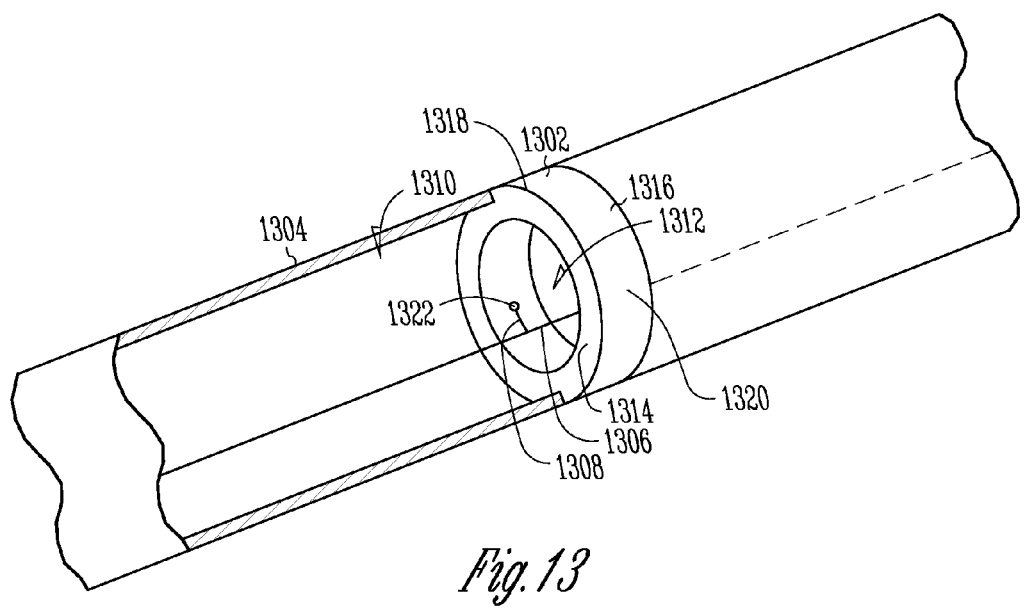
FIG. 13 illustrates a partially cut-away perspective view of a lead including a ring electrode, according to an example.

FIG. 13 illustrates a partially cut-away perspective view of a lead including a ring electrode 1302, according to an example. Tip electrodes and other electrodes are possible in additional examples. The ring electrode 1302 is coupled to a lead 1304, defining an interior space 1310. A conductor 1306 extends through the interior space. The conductor 1306 is pictured without coils, but additional examples include coils or other configurations. The conductor 1306 is pictured including a pigtail 1308 which is coupled to the ring electrode 1302. A pigtail is a single conductor extending from the conductor 1306. In additional examples, a portion of the insulator covering conductor 1306 is removed, and the exposed portion is coupled to the electrode 1302, such as to provide for coupling without a pigtail. The electrode 1302 can include multiple terminal types for connection to a conductor, including pads, crimpable terminals, and other terminals.

The exterior of the electrode 1302 can comprise a surface which is wholly conductive, in some examples. In additional examples, only a portion of the exterior surface of the electrode 1302 is conductive. In some examples, the electrode 1302 includes a shocking surface 1320 which is not insulated, and a conductor connection portion 1322 which is not insulated, while the remainder of the electrode exterior is insulated. Other configurations are possible. The conductor 1306 can be coupled to the electrode 1302 using a number of techniques, including, but not limited to, soldering, laser welding, crimping, and other joining techniques. The conductor 1306 extends further down the lead 1304, but an example could also terminate the conductor 1306 at the electrode 1302.

The conductor 1306 can include a single wire, such as for communicating data and for transferring power. In additional examples, the conductor 1306 can include two wires, such as for communicating data and transferring power using a first conductor, and for providing a ground path with a second conductor. Examples including more than two isolated signal paths in the conductor 1306 are possible as well.

The ring electrode 1302 includes electronics. The electronics are hermetically sealed inside the ring electrode 1302, in some examples. Some examples locate electronics in a space inside the ring electrode 1302 and couple the electronics to the ring electrode 1302. Several techniques can be used to couple the electronics to the ring electrode 1302 including, but not limited to, forming electronics on an interior of the electrode 1302, such as by using chemical vapor deposition of silicon onto an interior surface of the ring electrode. Additional examples include potting the electronics inside the electrode 1302.

The electrode 1302 is generally cylindrical, and defines an aperture 1312. Some examples provide a generally U-shaped portion 1316 in which electronics are disposed. A planar lid 1314 is provided in some examples, and is sealed to the U-shaped portion 1316, in an example. A seal 1318 includes a laser weld, in various embodiments. The laser weld occurs at a butt joint, a step joint, a lap joint, or other joints, in various embodiments. In various embodiments, the seal is hermetic. Examples in which the electrode 1302 includes two mating cup-shaped halves are also included. In some embodiments, the electrode 1302 includes a first half which is approximately a mirror image of the second half, when viewed from a cross section taken perpendicular to a plane defined by a joint joining the first and second halves.

In some examples, electronics disposed in the electrode 1302 include an electrostimulation capacitor. The electrostimulation capacitor is charged using energy from the conductor 1306, in an example. Some examples are configured such that a first switch is located in the electrode 1302, the first switch configured to control conductivity between the conductor and the electrode 1302. Additional examples include a first controller circuit located in the electrode 1302. In some examples, the first controller is coupled to the conductor 1306 and includes a first multiplexer circuit configured to multiplex over the conductor 1306 a first signal and a second signal, the first controller circuit configured to control the first switch based at least on the first signal.

Figure 14:
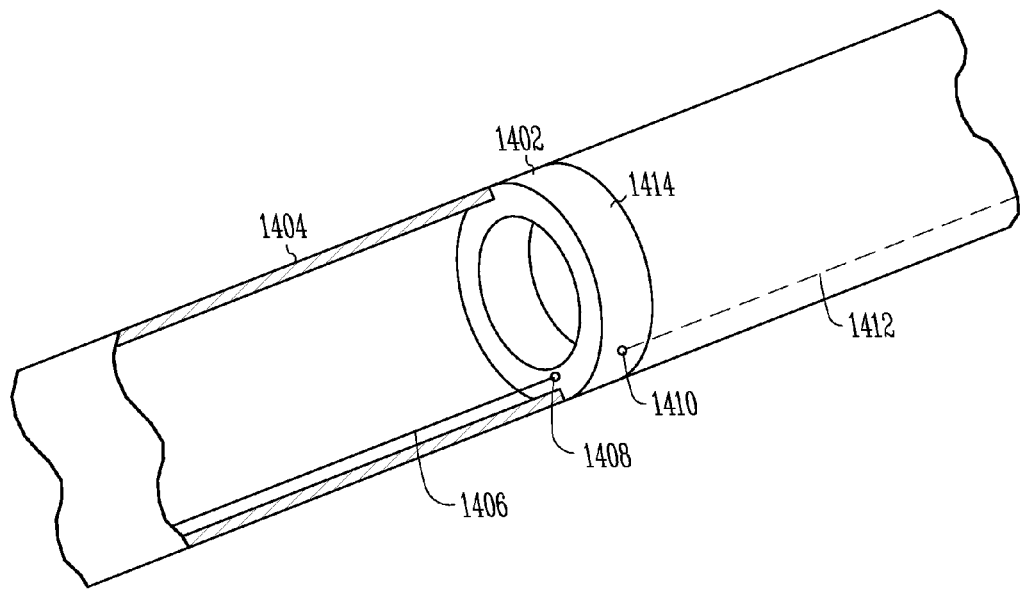
FIG. 14 illustrates a partially cut-away perspective view of a lead including a ring electrode, according to an example.

FIG. 14 illustrates a partially cut-away perspective view of a lead including a ring electrode, according to an example. A ring electrode 1402 is pictured. The ring electrode 1402 is coupled to a lead 1404, defining an interior space 1410. A conductive path is illustrated, including first conductor 1406, second conductor 1412, and the ring electrode 1402. The ring electrode 1402 is configured such that an insulated electric path extends through the ring electrode and couples portion 1408 to portion 1410 without putting the ring electrode shocking surface 1414 in direct electrical communication with portions 1408 and 1410. In some examples, coupling portions 1408 and 1410 are in direct conductive communication with the shocking surface 1414.

The conductor 1406 is pictured including a pigtail 1408 which is coupled to the ring electrode 1402. The conductor 1406 can be coupled to the electrode 1402 using a number of techniques, including, but not limited to, soldering, laser welding, crimping, and other joining techniques. The conductor 1406 extends further down the lead 1404, but an example could also terminate the conductor 1406 at the electrode 1402.

Figure 15:
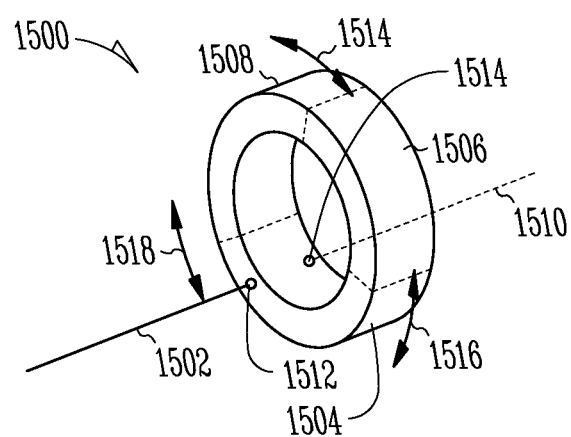
FIG. 15 illustrates a perspective view of a ring electrode able to stimulate multiple electrode surfaces, according to an example.

FIG. 15 illustrates a perspective view of a ring electrode 1500 able to stimulate multiple electrode surfaces, according to an example. The electrode 1500 is coupled to a conductor 1502 at first coupling portion 1512. An optional conductor 1510 is illustrated coupled to the electrode 1500 on a second coupling portion 1514 opposite the first coupling portion 1512. The first 1502 and second 1510 conductors are shown configured in a substantially coaxial arrangement. Additional examples arrange the conductors so they are not coaxial.

The electrode is configured such that it has multiple shocking surfaces. A first surface 1504 is illustrated along with a second surface 1506 and a third surface 1508. Although three surfaces are shown, some examples include two shocking surfaces, and additional examples include more than three shocking surface. The exterior of the ring electrode is configured such that the first 1504, second 1506, and third 1508 shocking surfaces are electrically isolated from one another, such as by coating, molding, or another configuration.

One or more of the first 1504, second 1506, and third 1508 shocking surfaces can be provided with an electrostimulation pulse to electrostimulate tissue. In some examples, electronics located in the electrode 1500 coordinate when an electrostimulation pulse is provided to one or more of the first 1504, second 1506, and third 1508 shocking surfaces. Such coordination can provide for adaptation of an electrostimulation pulse. For example, if it is determined that a pacing pulse which travels along vector 1514 causes capture, while a pacing pulse which travels along pacing vector 1516 does not cause capture, electrode surfaces 1508 and 1506 can be selected for pacing therapy. In some examples, electronics disposed in the electrode 1500 are configured such that the efficacy of shocking via one or more of the first 1504, second 1506, and third 1508 shocking surfaces is recorded and analyzed. Such examples can provide for automatic selection of one or more of the first 1504, second 1506, and third 1508 shocking surfaces.

Some examples provide for a manual configuration of the activation of one or more of the first 1504, second 1506, and third 1508 shocking surfaces. For example, in some examples, selection of one or more of the first 1504, second 1506, and third 1508 shocking surfaces for electrostimulation results in an unwanted side effect, such as stimulation of the phrenic nerve. To avoid such unwanted stimulation, less than all electrodes can be selected to provide stimulation. For example, stimulation can be provided by selectively activating only one of the first 1504, second 1506, and third 1508 shocking surfaces. Two or more surfaces can also be used.

Figure 16:
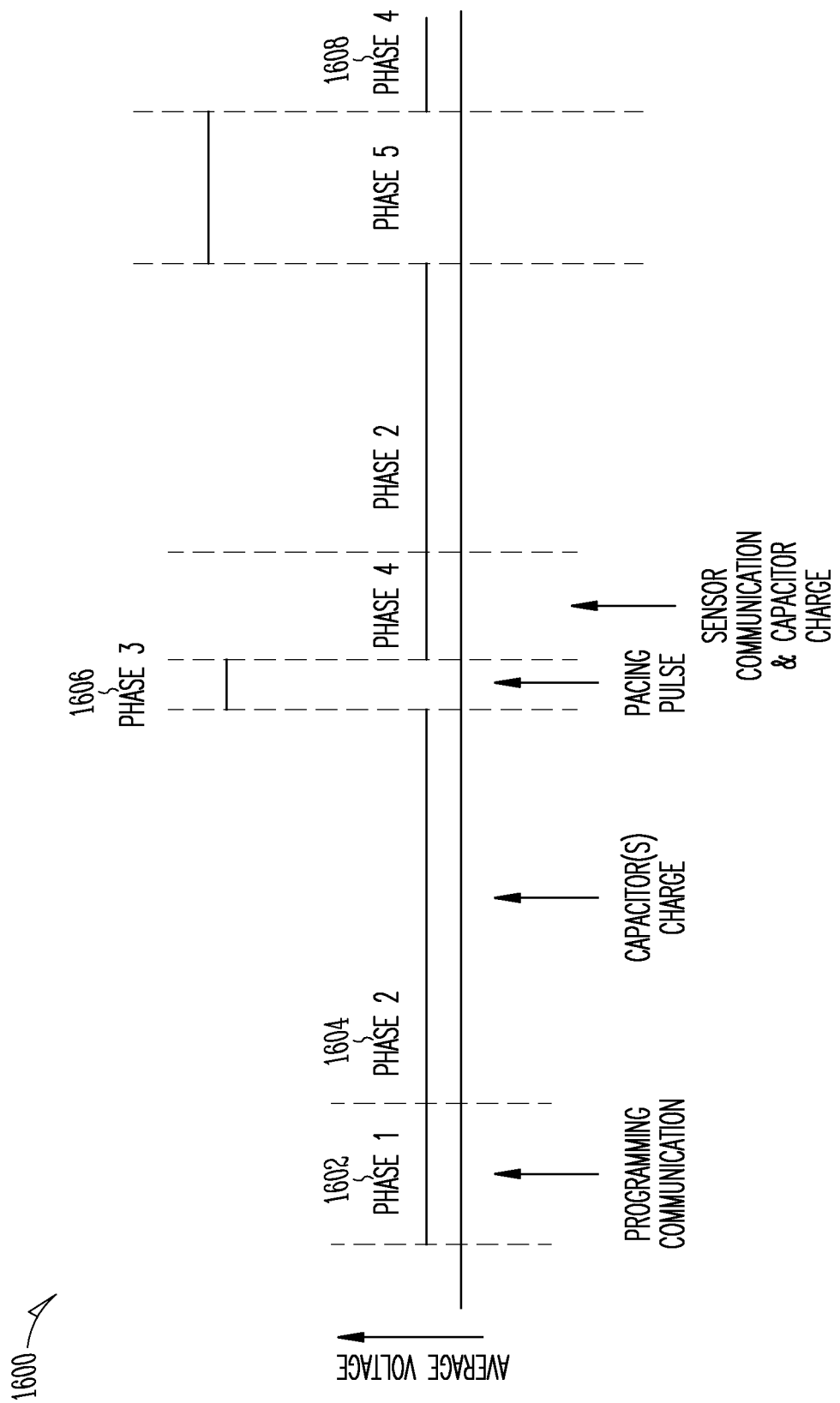
FIG. 16 illustrates a diagram of electronics in a lead, according to one example.

FIG. 16 illustrates a therapy method, according to one example. The present subject matter provides improved performance of lead based pacing therapy. This timing sequence 1600 includes a first phase 1602, a second phase 1604, a third phase 1606 and a fourth phase 1608. Average voltage is indicated by horizontal lines. The magnitude of this voltage is indicated along the Y axis. The present diagram is for explanation, and is not limited to DC voltage or average voltage.

During phase 1 1602, a communication signal from an implantable medical device is transmitted from the implantable medical device to electronics in a lead, such as electronics connected to one or more of a controller circuit, a shocking electrode, and a sensor. During phase 2 1604, a charge signal is transmitted from the implantable medical device to a capacitor located in the lead and controlled by the electronics located in the lead. During phase 3 1606, a shock occurs wherein the electronics switch the capacitor in the lead into conductivity with tissue. This voltage is not between an implantable medical device and electronics in a lead; it is between a shocking capacitor and tissue. Phase 4 1608 is a phase during that sensor information that has been recorded during any of phases 1-3 is transmitted from electronics in a lead to an implantable medical device. During this phase, a capacitor charge signal charges the shocking capacitor that was discharged during phase 3 1606. As illustrated phases 1-4 are repeated.

The illustration shows that one or more phases are not repeated in sequence. In certain examples, this is because some processes store programs in electronics in the leads so that the leads can monitor patient health by monitoring the tissue they are in communication with. These electronics can administer therapy to that tissue if a measurement does not indicate that an unrecognized situation is occurring. For example, extensive sensor data is collected by a more powerful processor in an implantable medical device, and is analyzed to select a patient therapy. A program representative of that therapy is communicated to electronics in a lead. To maintain small lead size, a small processor that is capable of reduced analysis is selected for the lead and receives the program. This processor is part of a system that is able to administer shocks and collect sensor data over time, so long as the sensor data does not trigger a flag. If the sensor data does not trigger a flag, programming is not needed. The illustrated example does not trigger a reprogramming flag, so phase 1 is not repeated.

The program illustrated recognizes that a longer pulse is needed. As such, phase 5 administers such a pulse. Phase 4 is repeated so that information related to the longer pulse can be transmitted to an implantable medical device. The implantable medical device can monitor electronics in the lead passively in this manner. The communication of sensor date to the implantable medical device is muted until a flag that increased analysis is needed, in some examples.

Figure 17:
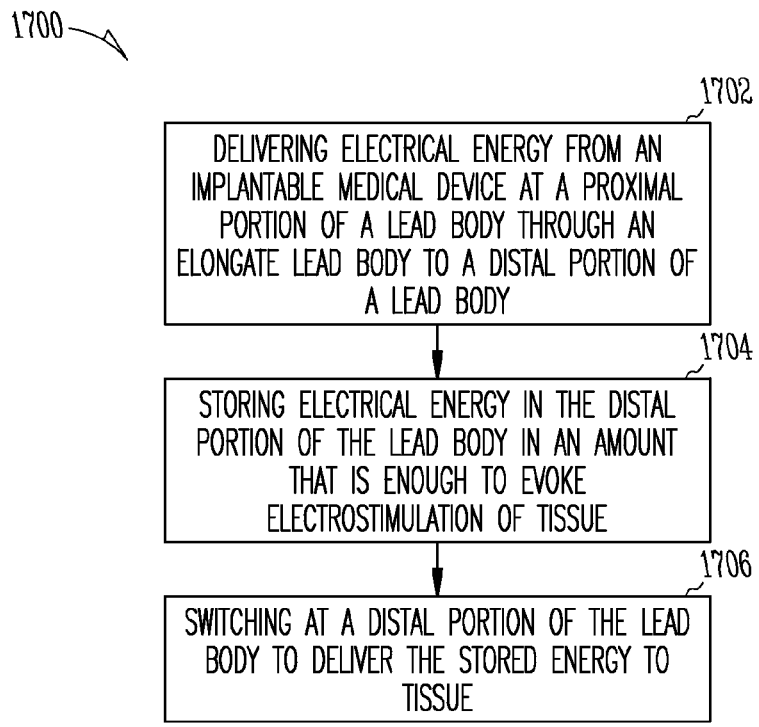
FIG. 17 illustrates a process for providing a therapy, according to one example.

FIG. 17 illustrates a process 1700 for providing a therapy, according to one example. At 1702, some examples of the present subject matter include delivering electrical energy from an implantable medical device at a proximal portion of a lead body through an elongate lead body to a distal portion of a lead body. Some of these embodiments include a conductor located in the lead body and extending from the proximal portion to the distal portion that conducts energy from the power source and through the lead body. At 1704, some examples include storing electrical energy, at a location that is at the distal portion of the lead body, in an amount that is enough to evoke electrostimulation of tissue. At 1706, some examples include switching, at the distal portion of the lead body, to deliver the stored energy to tissue. This switching is selective in some examples, occurring in response to a specified input such as a signal from a program in the switch or from a master device controlling the switch. In certain instances, the switch is part of a computer such as an integrated circuit including a controller circuit, a memory to store programs, and a switch, with the memory configured to store a program, and the controller circuit configured to read the memory and to control the switch.

Various options are included, such as selectively switching, at the distal portion of the lead body, to switch a sensor into communication with the tissue to provide sensor information to the implantable medical device. Some examples include storing the sensor information in a sensor buffer circuit located at the distal portion of the lead body. Some examples include communicating encoded information from the implantable medical device to a control circuit that is located at the distal portion of the lead. Some of these examples use the information at the control circuit to control the selectively switching, at the distal portion of the lead body, to deliver the stored energy to tissue.

Certain instances include storing electrical energy, at a location that is at the distal portion of the lead body, in an amount that is enough to power the control circuit during a time when the control circuit is unconnected to the implantable medical device.

Some examples include sharing a conductor, extending between proximal and distal portions of an elongate lead body, for (1) communicating encoded information from the implantable medical device to a location at the distal portion of the lead and (2) charging a capacitor located at the distal portion of the lead.

Figure 18:
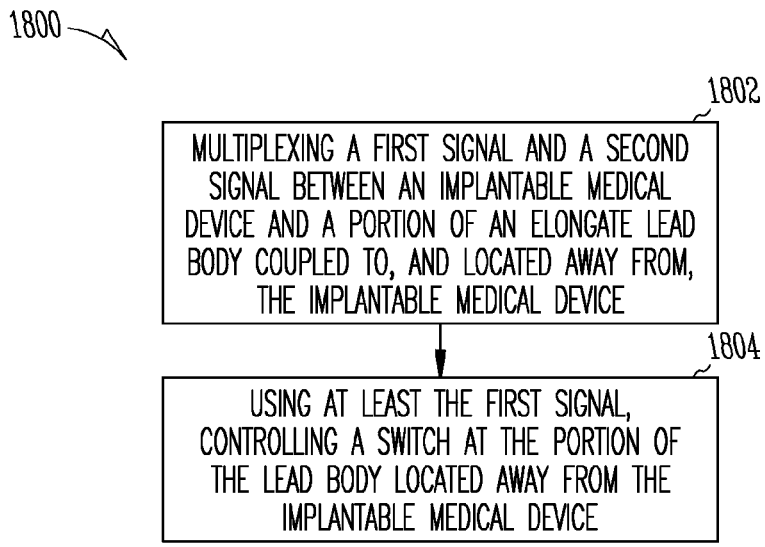
FIG. 18 illustrates a process for providing a therapy, according to one example.

FIG. 18 illustrates a process 1800 for providing a therapy, according to one example. At 1802, the example includes multiplexing a first signal and a second signal between an implantable medical device and a portion of an elongate lead body coupled to, and located away from, the implantable medical device. At 1804, the example includes using at least the first signal, controlling a switch at the portion of the lead body located away from the implantable medical device.

Some of these examples include optional methods. For instance, some methods use at least the first signal, controlling the switching at the portion of the lead body located away from the implantable medical device for transmitting a defibrillation pulse from the implantable medical device to a first electrode located at the portion of the lead body located away from the implantable medical device. Some examples power a first controller circuit, located at the portion of the lead body located away from the implantable medical device, using energy stored at the portion of the lead body located away from the implantable medical device, the powering occurring when the first controller circuit is decoupled from the implantable medical device. Some examples include multiplexing simplex communications. Some examples include multiplexing duplex communications.

Certain examples use the first signal to control switching, at a location on the elongate lead body located away from the implantable medical device, to deliver charge from the implantable medical device to a first electrostimulation capacitor located on the lead body away from the implantable medical device. Some of these examples use the first signal to control switching, at a location on the elongate lead body located away from the implantable medical device, to discharge energy from the electrostimulation capacitor. In some examples, the first signal includes information to control pacing.

Some examples are included in which the first signal and the second signal to a second controller circuit located on the lead body away from the implantable medical device. Some of these examples use at least the first signal and the second controller circuit, controlling a switching on the lead body away from the implantable medical device. In some examples, multiplexing includes communicating a pulse synchronization information from the implantable medical device to the first controller circuit and the second controller circuit using the first signal. Certain instances use the pulse synchronization information for controlling switching of first and second switches located on the lead body away from the implantable medical device.

Certain examples include switching the first switch and the second switch at a delay specified in the pulse synchronization information. Some of these examples include populating a pacing vector table according to one or more depolarizations sensed by a sensor. Some examples include comparing the pacing vector table to a specified pacing vector table. Some of these examples include switching the first switch and the second switch based on the comparison of the pacing vector table and the specified pacing vector table. Certain instances include switching, at the implantable medical device, to control conductivity to a third electrode of the implantable medical device such that a pacing vector extends between at least the first and third electrodes.

Figure 19:
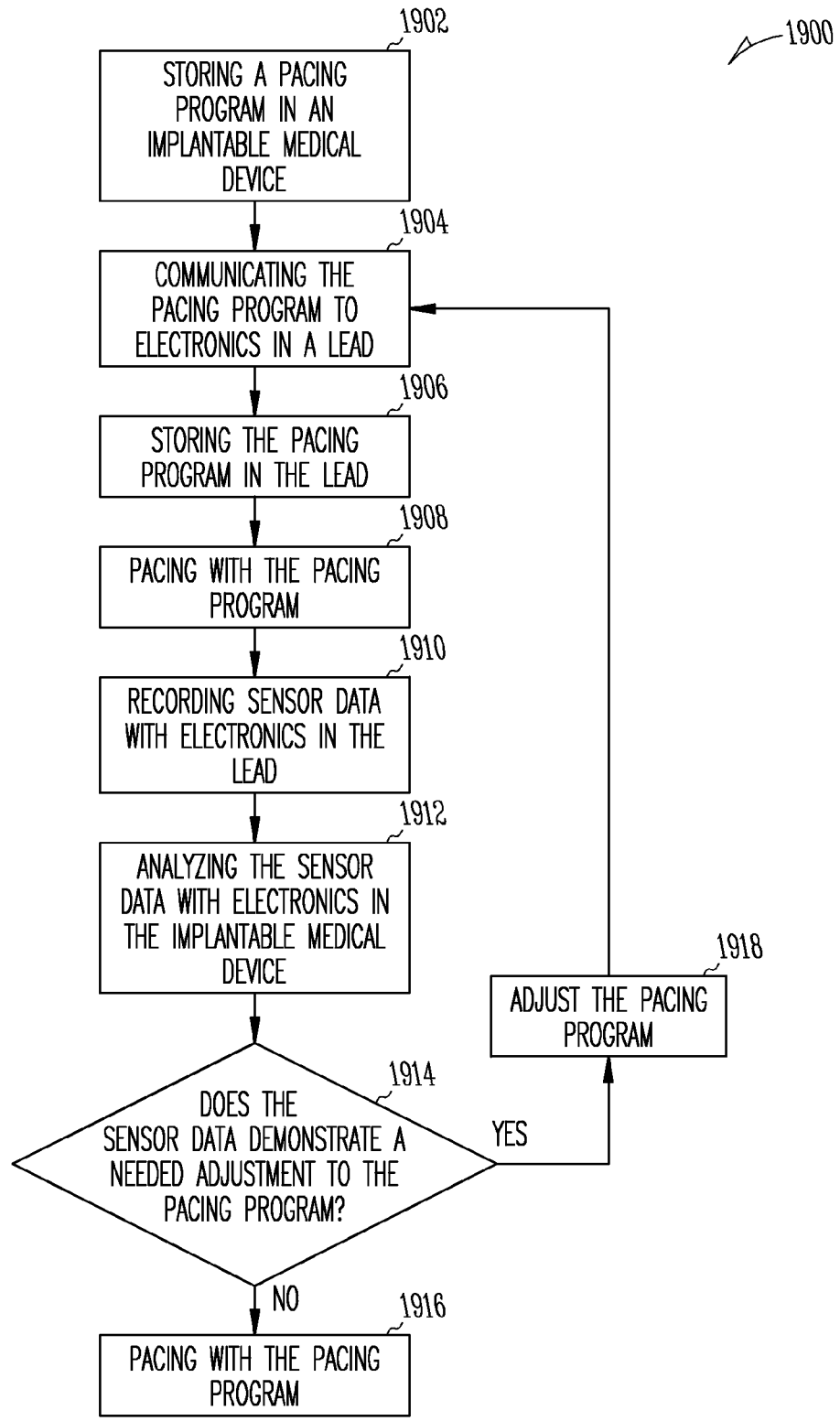
FIG. 19 illustrates a process for providing a therapy, according to one example.

FIG. 19 illustrates a process for providing a therapy, according to one example. At 1902, the example includes storing a pacing program in an implantable medical device. At 1904, the example includes communicating the pacing program to electronics in a lead. At 1906, the example includes storing the pacing program in the lead. At 1908, the example includes pacing with the pacing program. At 1910, the example includes recording sensor data with electronics in the lead. At 1912, the example includes analyzing the sensor data with electronics in the implantable medical device. At 1914, the example queries if the sensor data demonstrates a needed adjustment to the pacing program. At 1918, the example includes adjusting with the pacing program if adjustment is needed. At 1916, the example does not adjust the pacing program, and instead paces with the pacing program that was communicated at 1904.

Additional Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    an implantable lead, comprising an elongate lead body comprising a proximal portion and a distal portion, the lead comprising:
        a coupler, located at the proximal portion of the elongate lead body, the coupler configured to couple to an implantable medical device;
        a first conductor, coupled to the coupler, and extending away from the coupler at least partially through the lead along the elongate lead body;
        a first electrode, located on the lead away from the coupler;
        a first switch, located on the lead away from the coupler, the first switch configured to control conductivity between the conductor and the electrode; and
        a first controller circuit, located on the lead away from the coupler, the first controller circuit coupled to the conductor and including a first multiplexer circuit configured to multiplex over the conductor a first signal and a second signal, the first controller circuit configured to control the first switch based at least on the first signal.

2. The apparatus of claim 1, wherein the lead body comprises only one conductor extending from the proximal portion of the lead body to the distal portion of the lead body.

3. The apparatus of claim 1, comprising a sensor, located at the distal portion of the lead body and coupled to the first controller circuit, wherein the first signal includes sensor information associated with the sensor.

4. The apparatus of claim 1, comprising a second switch configured to control conductivity between the conductor and a second electrode.

5. The apparatus of claim 4, comprising a second controller circuit coupled to the conductor and including a second multiplexer circuit configured to multiplex over the conductor the first signal and the second signal, the second controller circuit configured to control the second switch based at least on the first signal.

6. The apparatus of claim 1, wherein the first controller circuit is configured to control the first switch based at least on the first signal, wherein the first signal includes a pulse delivery program.

7. The apparatus of claim 6, wherein the first controller circuit includes a timer circuit, and wherein the pulse delivery program includes a specified delay used by the timer to control the first switch.

8. The apparatus of claim 6, wherein the first controller circuit includes a timer circuit, and wherein the pulse delivery program is used by the timer to control the first switch.

9. The apparatus of claim 6, wherein the first multiplexer circuit is configured to provide the second signal that includes a charging signal for an electrostimulation capacitor located on the lead.

10. The apparatus of claim 1, comprising a decoupling circuit to decouple the first controller circuit from the implantable medical device when the first controller is in a powered state.

11. The apparatus of claim 4, comprising:
    a first decoupling circuit to decouple the first controller circuit from the implantable medical device when the first controller is in a powered state;
    a second controller circuit coupled to the conductor and including a second multiplexer circuit configured to multiplex over the conductor the first signal and the second signal, the second controller circuit configured to control the second switch based at least on the first signal; and
    a second decoupling circuit to decouple the second controller circuit from the implantable medical device when the second controller is in a powered state.

12. The apparatus of claim 4, wherein the lead body comprises only one conductor extending from the proximal portion of the lead body to the first controller.

13. The apparatus of claim 12, comprising a second controller circuit coupled to the conductor and including a second multiplexer circuit configured to multiplex over the conductor the first signal and the second signal, the second controller circuit configured to control the second switch based at least on the first signal, wherein the only one conductor extends from the proximal portion of the lead body to the second controller.

14. The apparatus of claim 1, comprising a ring electrode including the first shocking surface and a second shocking surface, electrically isolated from one another, each coupled to the first switch.

15. A method, comprising:
    multiplexing a first signal and a second signal for conduction between an implantable medical device and a portion of an elongate lead body coupled to, and located away from, the implantable medical device; and
    controlling, with a first controller circuit operating in association with the first signal, a switching at the portion of the lead body located away from the implantable medical device;

providing the first signal and the second signal to a second controller circuit located on the lead body away from the implantable medical device; and using at least the first signal and the second controller circuit to control switching on the lead body away from the implantable medical device.

16. The method of claim 15, comprising:

using at least the first signal, controlling the switching at the portion of the lead body located away from the implantable medical device for transmitting an electrostimulation or defibrillation energy from the implantable medical device to a first electrode located at the portion of the lead body located away from the implantable medical device.

17. The method of claim 15, comprising:

powering the first controller circuit, located at the portion of the lead body located away from the implantable medical device, using energy stored at the portion of the lead body located away from the implantable medical device using the second signal, the powering occurring when the first controller circuit is decoupled from the implantable medical device.

18. The method of claim 17, wherein the multiplexing includes simplex communication.

19. The method of claim 17, wherein the multiplexing includes duplex communication.

20. The method of claim 15, comprising:

using the first signal to control switching, at a location on the elongate lead body located away from the implantable medical device, to deliver charge from the implantable medical device to a first electrostimulation capacitor located on the lead body away from the implantable medical device; and using the first signal to control switching, at a location on the elongate lead body located away from the implantable medical device, to discharge energy from the electrostimulation capacitor.

21. The method of claim 20, comprising using the first signal to provide information to control pacing.

22. The method of claim 15, wherein the multiplexing comprises:

communicating a pulse synchronization information from the implantable medical device to the first controller circuit and the second controller circuit using the first signal; and using the pulse synchronization information to control switching of a first switch and a second switch located on the lead body away from the implantable medical device.

23. The method of claim 22, comprising switching the first switch and the second switch at a delay specified in the pulse synchronization information.

24. The method of claim 15, comprising:

populating a pacing vector table according to one or more sensed depolarizations;

comparing the pacing vector table to a specified pacing vector table; and switching a first switch and a second switch based on a comparison of the pacing vector table and the specified pacing vector table.

25. The method of claim 24, comprising:

switching, at the implantable medical device, to control conductivity to a third electrode of the implantable medical device such that a pacing vector extends between at least the first and third electrodes.

* * * * *

UNITED STATES PATENT AND TRADEMARK OFFICE
CERTIFICATE OF CORRECTION

| | | |
|---|---|---|
| PATENT NO. | : 8,914,130 B2 | Page 1 of 1 |
| APPLICATION NO. | : 12/233345 | |
| DATED | : December 16, 2014 | |
| INVENTOR(S) | : Wulfman | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1329 days.

Signed and Sealed this
Twenty-seventh Day of October, 2015

Michelle K. Lee
*Director of the United States Patent and Trademark Office*